(12) United States Patent
Bös et al.

(10) Patent No.: US 6,274,588 B1
(45) Date of Patent: Aug. 14, 2001

(54) 4-PHENYL-PYRIMIDINE DERIVATIVES

(75) Inventors: Michael Bös, Montreal (CA); Guido Galley, Rheinfelden (DE); Thierry Godel, Basel (CH); Torsten Hoffmann, Birsfelden (CH); Walter Hunkeler, Magden (CH); Patrick Schnider, Oberwil (CH); Heinz Stadler, Rheinfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/575,382

(22) Filed: May 22, 2000

(30) Foreign Application Priority Data

May 31, 1999 (EP) .................................. 99110483

(51) Int. Cl.$^7$ ........................ C07D 239/24; A61K 31/505
(52) U.S. Cl. .................. 514/269; 514/235.8; 514/237.2; 514/252.14; 514/272; 514/274; 514/275; 514/256; 544/324; 544/323; 544/322; 544/317; 544/316; 544/315; 544/122; 544/296; 544/295
(58) Field of Search .................................. 544/335, 327, 544/328, 329, 333, 295, 296, 122, 315; 514/235.8, 269, 275

(56) References Cited

U.S. PATENT DOCUMENTS

| | | | |
|---|---|---|---|
| 4,783,459 | * 11/1988 | Buhmann et al. | 514/235.8 |
| 5,516,775 | * 5/1996 | Zimmermann et al. | 514/224.2 |
| 5,972,938 | 10/1999 | Rupniak | 514/236.2 |

FOREIGN PATENT DOCUMENTS

| | | |
|---|---|---|
| 169 712 | 1/1986 | (EP) . |
| WO 95/18124 | 7/1995 | (WO) . |
| 97/09315 | 3/1997 | (WO) . |

OTHER PUBLICATIONS

Neurosci. Res., 1996, 7, 187–214, Barker.
Can. J. Phys., 1997, 75, 612–621, Longmore et al.
Science, 1998, 281, 1640–1645, Kramer et al.
Tachykinin Receptor and Tachykinin Antagonists, J. Auton. Pharmacol., 13, 23–93, 1993.

* cited by examiner

Primary Examiner—John M. Ford
(74) Attorney, Agent, or Firm—George W. Johnston; Patricia S. Rocha-Tramaloni; Eileen M. Ebel

(57) ABSTRACT

The invention provides compounds of the formula

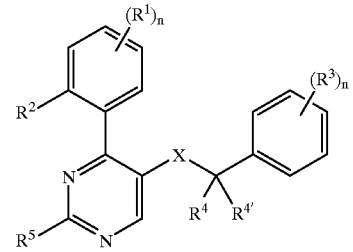

I wherein
$R^1$ is hydrogen or halogen;
$R^2$ is hydrogen, halogen, lower alkyl or lower alkoxy;
$R^1$ and $R^2$ may together be —CH=CH—CH=CH—, wherein R1 and $R^2$ together with the two carbon ring atoms to which they are attached form a fused ring;
$R^3$ is halogen, trifluoromethyl, lower alkyl or lower alkoxy;
$R^4/R^{4'}$ are each independently hydrogen or lower alkyl;
$R^5$ is lower alkyl, lower alkoxy, amino, phenyl, hydroxy-lower alkyl, cyano-lower alkyl, carbamoyl-lower alkyl, pyridyl, pyrimidyl, —(CH$_2$)$_n$-piperazinyl, which is optionally substituted by one or two lower alkyl groups or by hydroxy-lower alkyl, —(CH$_2$)$_n$-morpholinyl, —(CH$_2$)$_n$-piperidinyl, —(CH$_2$)$_{n+1}$-imidazolyl, lower alkyl-sulfanyl, lower alkyl-sulfonyl, benzylamino, —NH—(CH$_2$)$_{n+1}$N(R$^{4''}$)$_2$, —(CH$_2$)$_{n+1}$N(R$^{4''}$)$_2$, —O—(CH$_2$)$_{n+1}$-morpholinyl, —O—(CH$_2$)$_{n+1}$-piperidinyl or —O—(CH$_2$)$_{n+1}$N(R$^{4''}$)$_2$, wherein R$^{4''}$ is hydrogen or lower alkyl; and
n is 0–2;
X is —C(O)N(R$^{4''}$)— or —N(R$^{4''}$)C(O)—;
and to pharmaceutically acceptable acid addition salts thereof.

It has been shown that the compounds have a good affinity to the NK-1 receptor and may therefore used for the treatment of diseases related to this receptor.

11 Claims, No Drawings

4-PHENYL-PYRIMIDINE DERIVATIVES

BACKGROUND OF THE INVENTION

Substance P is a naturally occurring undecapeptide belonging to the tachykinin family of peptides, the latter being so-named because of their prompt contractile action on extravascular smooth muscle tissue. The receptor for substance P is a member of the superfamily of G protein-coupled receptors.

The neuropeptide receptors for substance P (NK-1) are widely distributed throughout the mammalian nervous system (especially brain and spinal ganglia), the circulatory system and peripheral tissues (especially the duodenum and jejunum) and are involved in regulating a number of diverse biological processes.

The central and peripheral actions of the mammalian tachykinin substance P have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (Neurosci. Res., 1996, 7, 187–214), anxiety (Can. J. Phys., 1997, 75, 612–621) and depression (Science, 1998, 281, 1640–1645).

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, is reviewed in "Tachykinin Receptor and Tachykinin Receptor Antagonists", J. Auton. Pharmacol., 13, 23–93, 1993.

Furthermore, Neurokinin 1 receptor antagonists are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

The neurokinin-1 receptor antagonists are further useful for the treatment of motion sickness and for treatment induced vomiting.

In addition, in The New England Journal of Medicine, Vol. 340, No. 3 190–195, 1999 has been described the reduction of cisplatin-induced emesis by a selective neurokinin-1-receptor antagonist.

Furthermore, U.S. Pat. No. 5,972,938 describes a method for treating a psychoimmunologic or a psychosomatic disorder by administration of a tachykinin receptor antagonist, such as NK-1 receptor antagonist.

SUMMARY OF THE INVENTION

The present invention relates to compounds of the formula

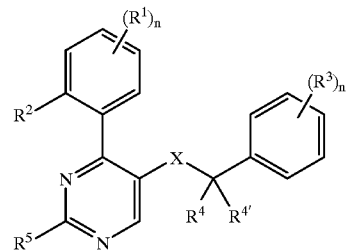

wherein
$R^1$ is hydrogen or halogen;
$R^2$ is hydrogen, halogen, lower alkyl or lower alkoxy;
$R^1$ and $R^2$ may together be —CH=CH—CH=CH—, wherein $R^1$ and $R^2$ together with the two carbon ring atoms to which they are attached form a fused ring;
$R^3$ is halogen, trifluoromethyl, lower alkyl or lower alkoxy;
$R^4$ and $R^{4'}$ are each independently hydrogen or lower alkyl;
$R^5$ is lower alkyl, lower alkoxy, amino, phenyl, hydroxy-lower alkyl, cyano-lower alkyl, carbamoyl-lower alkyl, pyridyl, pyrimidyl, —(CH$_2$)$_n$-piperazinyl which is optionally substituted by one or two lower alkyl groups or by hydroxy-lower alkyl, —(CH$_2$)$_n$-morpholinyl, —(CH$_2$)$_n$-piperidinyl, —(CH$_2$)$_{n+1}$-imidazolyl, lower alkyl-sulfanyl, lower alkyl-sulfonyl, benzylamino, —NH—(CH$_2$)$_{n+1}$N(R$^{4''}$)$_2$, —(CH$_2$)$_{n+1}$N(R$^{4''}$)$_2$, —O—(CH$_2$)$_{n+1}$-morpholinyl, —O—(CH$_2$)$_{n+1}$-piperidinyl or —O—(CH$_2$)$_{n+1}$N(R$^{4''}$)$_2$, wherein $R^{4''}$ is hydrogen or lower alkyl; and
n is 0–2;
X is —C(O)N(R$^{4''}$)— or —N(R$^{4''}$)C(O)—;
and to pharmaceutically acceptable acid addition salts thereof.

The compounds of formula I and their salts are characterized by valuable therapeutic properties. It has been surprisingly found that the compounds of the present invention are antagonists of the Neurokinin 1 (NK-1, substance P) receptor.

DETAILED DESCRIPTION OF THE INVENTION

The present invention relates to compounds of the formula

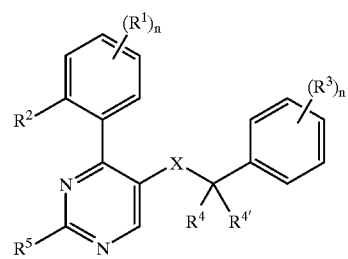

wherein
$R^1$ is hydrogen or halogen;
$R^2$ is hydrogen, halogen, lower alkyl or lower alkoxy;
$R^1$ and $R^2$ may together be —CH=CH—CH=CH—, wherein $R^1$ and $R^2$ together with the two carbon ring atoms to which they are attached form a fused ring;

$R^3$ is halogen, trifluoromethyl, lower alkyl or lower alkoxy;

$R^4$ and $R^{4'}$ are each independently hydrogen or lower alkyl;

$R^5$ is lower alkyl, lower alkoxy, amino, phenyl, hydroxy-lower alkyl, cyano-lower alkyl, carbamoyl-lower alkyl, pyridyl, pyrimidyl, —$(CH_2)_n$-piperazinyl which is optionally substituted by one or two lower alkyl groups or by hydroxy-lower alkyl, —$(CH_2)_n$-morpholinyl, —$(CH_2)_n$-piperidinyl, —$(CH_2)_{n+1}$-imidazolyl, lower alkyl-sulfanyl, lower alkyl-sulfonyl, benzylamino, —NH—$(CH_2)_{n+1}N(R^{4"})_2$, —$(CH_2)_{n+1}N(R^{4"})_2$, —O—$(CH_2)_{n+1}$-morpholinyl, —O—$(CH_2)_{n+1}$-piperidinyl or —O—$(CH_2)_{n+1}N(R^{4"})_2$, wherein $R^{4"}$ is hydrogen or lower alkyl; and n is 0–2;

X is —C(O)N($R^{4"}$)— or —N($R^{4"}$)C(O)—;

and to pharmaceutically acceptable acid addition salts thereof.

The compounds of formula I and their salts are characterized by valuable therapeutic properties. It has been surprisingly found that the compounds of the present invention are antagonists of the Neurokinin 1 (NK-1, substance P) receptor.

The present invention provides the compounds of formula I and pharmaceutically acceptable salts thereof, the preparation of the above-mentioned compounds, medicaments containing them and their manufacture as well as the use of the above-mentioned compounds in the control or prevention of illnesses, especially of illnesses and disorders of the kind referred to earlier or in the manufacture of corresponding medicaments.

The most preferred indications in accordance with the present invention are those which include disorders of the central nervous system, for example the treatment or prevention of certain depressive disorders or emesis by the administration of NK-1 receptor antagonists. A major depressive episode has been defined as being a period of at least two weeks during which, for most of the day and nearly every day, there is either depressed mood or the loss of interest or pleasure in all, or nearly all activities.

The following definitions of the general terms used in the present description apply irrespective of whether the terms in question appear alone or in combination. As used herein, the term "lower alkyl" denotes a straight- or branched-chain alkyl group containing from 1–7 carbon atoms, for example, methyl, ethyl, propyl, isopropyl, n-butyl, i-butyl, t-butyl and the like.

Preferred lower alkyl groups are groups with 1–4 carbon atoms.

The term "lower alkoxy" denotes a group wherein the alkyl residues are as defined above, and which is attached via an oxygen atom.

The term "halogen" denotes chlorine, iodine, fluorine and bromine.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Exemplary preferred compounds are those in which X is —C(O)N($R^{4"}$)—, wherein $R^{4"}$ is methyl, and $R^5$ is piperazinyl optionally substituted by one or two methyl groups, for example the following compounds:

4-(2-bromo-phenyl)-2-(4-methyl-piperazin-1-yl)-pyrimidine-5-carboxylic acid (3,5-bis-trifluoromethyl-benzyl)-methyl-amide, (3R,5S)-4-(2-bromo-phenyl)-2-(3,5-dimethyl-piperazin-1-yl)-pyrimidine-5-carboxylic acid (3,5-bis-trifluoromethyl-benzyl)-methyl-amide, 4-(2-bromo-phenyl)-2-piperazin-1-yl-pyrimidine-5-carboxylic acid (3,5-bis-trifluoromethyl-benzyl)-methyl-amide, 4-(2-chloro-phenyl)-2-(4-methyl-piperazin-1-yl)-pyrimidine-5-carboxylic acid (3,5-bis-trifluoromethyl-benzyl)-methyl-amide, (3R,5S)-4-(2-chloro-phenyl)-2-(3,5-dimethyl-piperazin-1-yl)-pyrimidine-5-carboxylic acid (3,5-bis-trifluoromethyl-benzyl)-methyl-amide, 4-(2-chloro-phenyl)-2-piperazin-1-yl-pyrimidine-5-carboxylic acid (3,5-bis-trifluoromethyl-benzyl)-methyl-amide, 2-(4-methyl-piperazin-1-yl)-4-o-tolyl-pyrimidine-5-carboxylic acid (3,5-bis-trifluoromethyl-benzyl)-methyl-amide, (3R,5S)-2-(3,5-dimethyl-piperazin-1-yl)-4-o-tolyl-pyrimidine-5-carboxylic acid (3,5-bis-trifluoromethyl-benzyl)-methyl-amide, 2-piperazin-1-yl-4-o-tolyl-pyrimidine-5-carboxylic acid (3,5-bis-trifluoromethyl-benzyl)-methyl-amide, 4-(2-methoxy-phenyl)-2-(4-methyl-piperazin-1-yl)-pyrimidine-5-carboxylic acid (3,5-bis-trifluoromethyl-benzyl)-methyl-amide, (3R,5S)-2-(3,5-dimethyl-piperazin-1-yl)-4-(2-methoxy-phenyl)-pyrimidine-5-carboxylic acid (3,5-bis-trifluoromethyl-benzyl)-methyl-amide, 4-(2-methoxy-phenyl)-2-piperazin-1-yl-pyrimidine-5-carboxylic acid (3,5-bis-trifluoromethyl-benzyl)-methyl-amide, 4-(4-fluoro-phenyl)-2-(4-methyl-piperazin-1-yl)-pyrimidine-5-carboxylic acid (3,5-bis-trifluoromethyl-benzyl)-methyl-amide, 4-(2-fluoro-phenyl)-2-(4-methyl-piperazin-1-yl)-pyrimidine-5-carboxylic acid (3,5-bis-trifluoromethyl-benzyl)-methyl-amide, (3R,5S)-2-(3,5-dimethyl-piperazin-1-yl)-4-(2-fluoro-phenyl)-pyrimidine-5-carboxylic acid (3,5-bis-trifluoromethyl-benzyl)-methyl-amide, 4-(4-fluor-phenyl)-2-piperazin-1-yl-pyrimidine-5-carboxylic acid (3,5-bis-trifluoromethyl-benzyl)-methyl-amide, 4-(4-fluoro-2-methyl-phenyl)-2-(4-methyl-piperazin-1-yl)-pyrimidine-5-carboxylic acid (3,5-bis-trifluoromethyl-benzyl)-methyl-amide, (3R,5S)-2-(3,5-dimethyl-piperazin-1-yl)-4-(4-fluoro-2-methyl-phenyl)-pyrimidine-5-carboxylic acid (3,5-bis-trifluoromethyl-benzyl)-methyl-amide, 4-(4-fluor-2-methyl-phenyl)-2-piperazin-1-yl-pyrimidine-5-carboxylic acid (3,5-bis-trifluoromethyl-benzyl)-methyl-amide, 2-(4-methyl-piperazin-1-yl)-4-naphthalen-1-yl-pyrimidine-5-carboxylic acid (3,5-bis-30 trifluoromethyl-benzyl)-methyl-amide, (3R,5S)-2-(3,5-dimethyl-piperazin-1-yl)-4-naphthalen-1-yl-pyrimidine-5-carboxylic acid (3,5-bis-trifluoromethyl-benzyl)-methyl-amide, 4-naphthalen-1-yl-2-piperazin-1-yl-pyrimidine-5-carboxylic acid (3,5-bis-trifluoromethyl-benzyl)-methyl-amide, 4-(2-chloro-4-fluoro-phenyl)-2-(4-methyl-piperazin-1-yl)-pyrimidine-5-carboxylic acid (3,5-bis-trifluoromethyl-benzyl)-methyl-amide, and 4-(2-chloro-4-fluoro-phenyl)-2-piperazin-1-yl-pyrimidine-5-carboxylic acid (3,5-bis-trifluoromethyl-benzyl)-methyl-amide.

Further preferred are compounds in which X is —C(O)N($R^{4"}$)—, wherein $R^{4"}$ is methyl and $R^5$ is morpholinyl or —O(CH$_2$)$_2$-morpholinyl.

Examples of such compounds are:
4-(2-bromo-phenyl)-2-morpholin-4-yl-pyrimidine-5-carboxylic acid (3,5-bis-trifluoromethyl-benzyl)-methyl-amide,
4-(2-chloro-phenyl)-2-morpholin-4-yl-pyrimidine-5-carboxylic acid (3,5-bis-trifluoromethyl-benzyl)-methyl-amide,
4-(2-chloro-phenyl)-2-(2-morpholin-4-yl-ethoxy)-pyrimidine-5-carboxylic acid (3,5-bis-trifluoromethyl-benzyl)-methyl-amide,
2-morpholin-4-yl-4-o-tolyl-pyrimidine-5-carboxylic acid (3,5-bis-trifluoromethyl-benzyl)-methyl-amide,
4-(2-methoxy-phenyl)-2-morpholin-4-yl-pyrimidine-5-carboxylic acid (3,5-bis-trifluoromethyl-benzyl)-methyl-amide,
4-(4-fluoro-2-methyl-phenyl)-2-morpholin-4-yl-pyrimidine-5-carboxylic acid (3,5-bis-trifluoromethyl-benzyl)-methyl-amide,
2-morpholin-4-yl-4-naphthalen-1-yl-pyrimidine-5-carboxylic acid (3,5-bis-trifluoromethyl-benzyl)-methyl-amide, and
4-(2-chloro-4-fluoro-phenyl)-2-morpholin-4-yl-pyrimidine-5-carboxylic acid (3,5-bis-trifluoromethyl-benzyl)-methyl-amide.

Preferred are further compounds, in which X is —C(O)N($R^{4"}$)—, $R^{4"}$ is methyl and $R^5$ is —NH(CH$_2$)$_2$N(CH$_3$)$_2$, —O(CH$_2$)$_2$N(CH$_3$)$_2$ or —O(CH$_2$)$_3$N(CH$_3$)$_2$, for example the following compounds:
4-(2-chloro-phenyl)-2-(2-dimethylamino-ethylamino)-pyrimidine-5-carboxylic acid (3,5-bis-trifluoromethyl-benzyl)-methyl-amide,
4-(2-chloro-phenyl)-2-(2-dimethylamino-ethoxy)-pyrimidine-5-carboxylic acid (3,5-bis-trifluoromethyl-benzyl)-methyl-amide,
4-(2-chloro-phenyl)-2-(3-dimethylamino-propoxy)-pyrimidine-5-carboxylic acid (3,5-bis-trifluoromethyl-benzyl)-methyl-amide,
2-(2-dimethylamino-ethoxy)-4-o-tolyl-pyrimidine-5-carboxylic acid (3,5-bis-trifluoromethyl-benzyl)-methyl-amide, and
2-(3-dimethylamino-propoxy)-4-o-tolyl-pyrimidine-5-carboxylic acid (3,5-bis-trifluoromethyl-benzyl)-methyl-amide.

Preferred are further compounds, in which X is —N($R^{4"}$)C(O)—, $R^{4"}$ is methyl and $R^5$ is morpholinyl or piperazinyl, otionally substituted by lower alkyl, for example the following compounds:
2-(3,5-bis-trifluoromethyl-phenyl)-N-methyl-N-[2-(4-methyl-piperazin-1-yl)-4-o-tolyl-pyrimidin-5-yl]-isobutyramide, and
2-(3,5-bis-trifluoromethyl-phenyl)-N-methyl-N-(2-morpholin-4-yl-4-o-tolyl-pyrimidin-5-yl)-isobutyramide.

The present compounds of formula I and their pharmaceutically acceptable salts can be prepared by methods known in the art, for example, by processes described below, which process comprises a) reacting a compound of formula

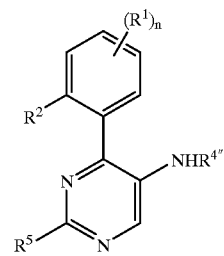

II with a compound of formula

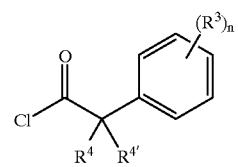

III to a compound of formula

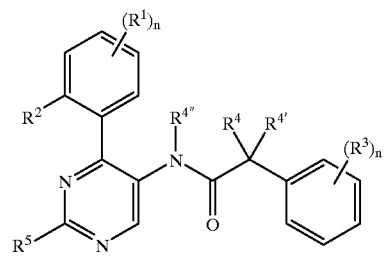

I-1 wherein $R^1$–$R^5$ and n have the significances given above, or b) reacting a compound of formula

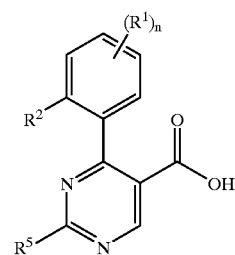

IV with a compound of formula

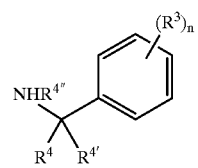

V to give a compound of formula

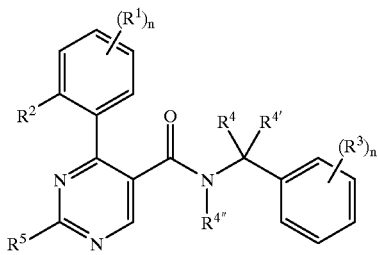

wherein $R^1$–$R^5$ and n have the significances given above, and optionally c) modifying one or more substituents $R^1$–$R^5$ within the definitions given above, and/or if desired, converting the compound obtained into a pharmaceutically acceptable acid addition salt.

In accordance with process variant a), to a compound of formula II, for example methyl-[6-(4-methyl-piperazin-1-yl)-4-o-tolyl-pyrimidin-3-yl]amine, a compound of formula III, for example 2-(3,5-bis-trifluoromethyl-phenyl)-2-methyl-propionyl chloride in dichloromethane, DIPEA (N-ethyidiisopropyl-amine), is added and the mixture is stirred at temperatures between 35–40° C. The desired compound of formula I-1 is obtained after purification in good yields.

Process variant b) describes the reaction of a compound of formula IV with a compound of formula V to a compound of formula I-2. The reaction is carried out in conventional manner, for example in a solvent, such as dichloromethane in presence of triethylamine, EDCI (N-(3-dimethylaminopropyl)-N'-ethyl-carbodiimide hydrochloride) and HOBT (1-hydroxy-benzotriazole). The mixture is stirred for about 12 hours at 20°.

The salt formation is effected at room temperature in accordance with methods which are known per se and which are familiar to any person skilled in the art. Not only salts with inorganic acids, but also salts with organic acids came into consideration. Hydrochlorides, hydrobromides, sulphates, nitrates, citrates, acetates, maleates, succinates, methan-sulphonates, p-toluenesulphonates and the like are examples of such salts.

The following schemes 1–6 describe the processes for preparation of compounds of formula I in more detail. The starting materials of formulae V, VIII, X, XIV and XVIII are known compounds and may be prepared according to methods known in the art.

In the schemes the following abbreviations have been used:

| | |
|---|---|
| THF | tetrahydrofuran |
| DIPEA | N-ethyldiisopropyl-amine |
| HOBT | 1-hydroxy-benzotriazole |
| EDCI | N-(3-dimethylaminopropyl)-N'-ethyl-carbodiimide hydrochloride |
| m-CPBA | m-chloroperbenzoic acid |
| DPPA | diphenylphosphorylazide |
| DMF | dimethylformamide |
| NEt₃ | triethylamine |

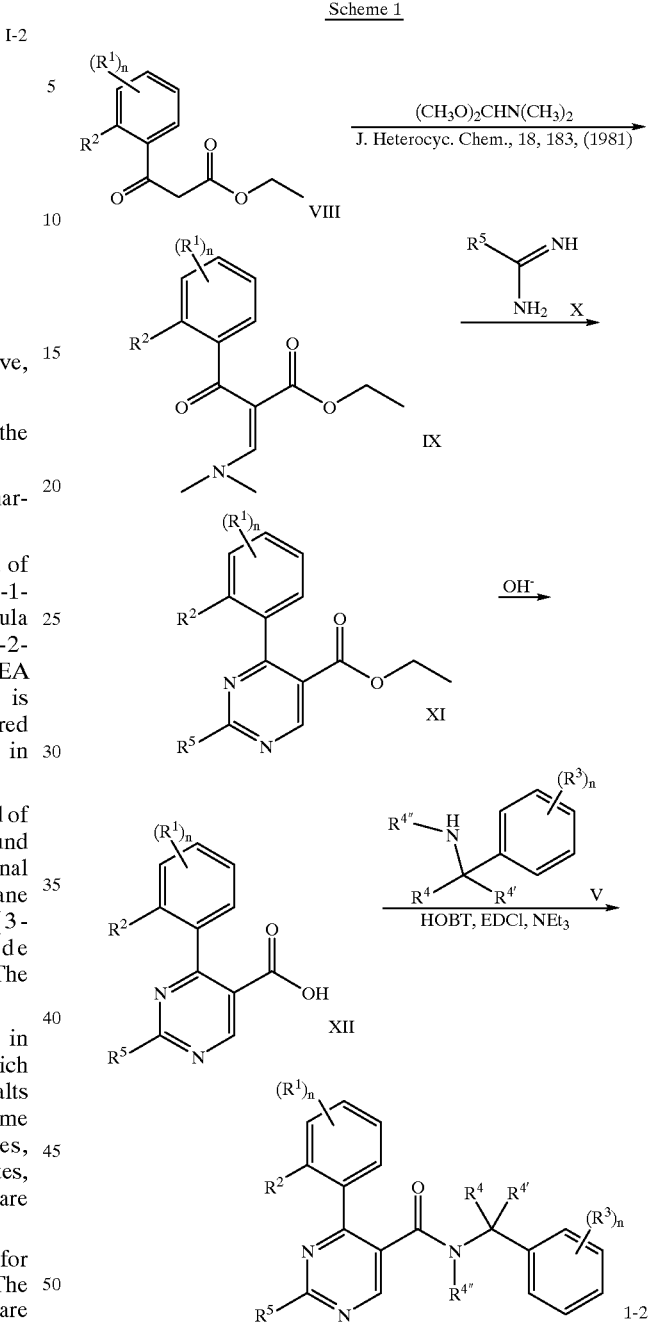

The substituents are given above.

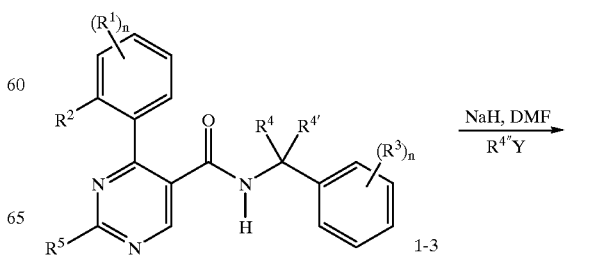

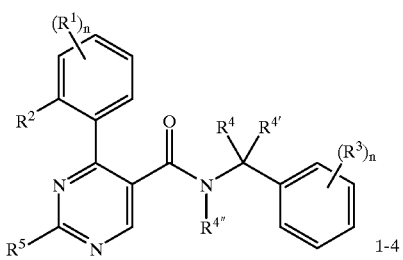
The substituents are given above.
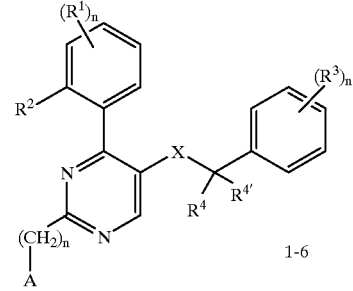
R' is lower alkyl and Y is halogen. A is an amine group such as —N(R$^4$)$_2$, piperazinyl, morpholinyl, piperidinyl or imidazolyl. The remaining substituents are given above.
Scheme 3
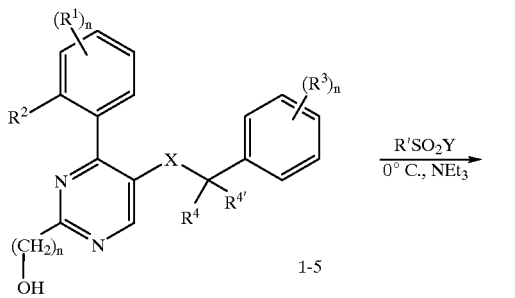
Scheme 4
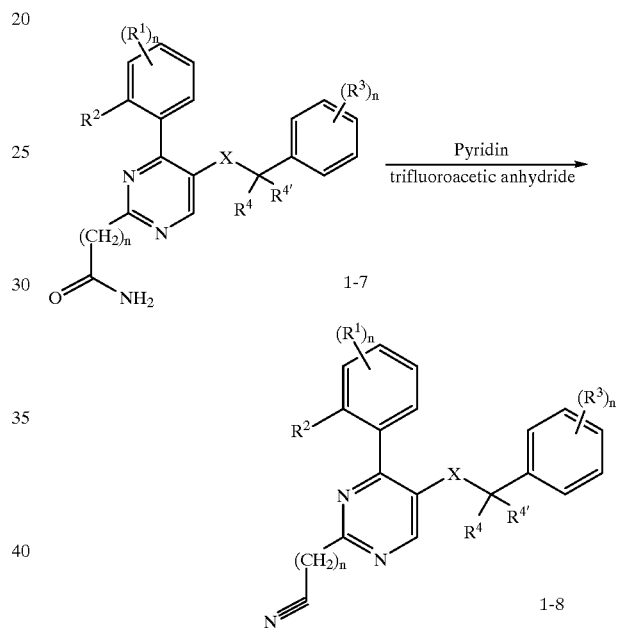
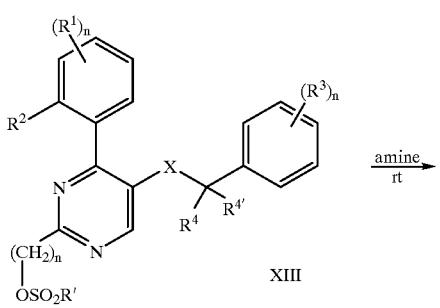
The definition of substituents is given above.
Scheme 5
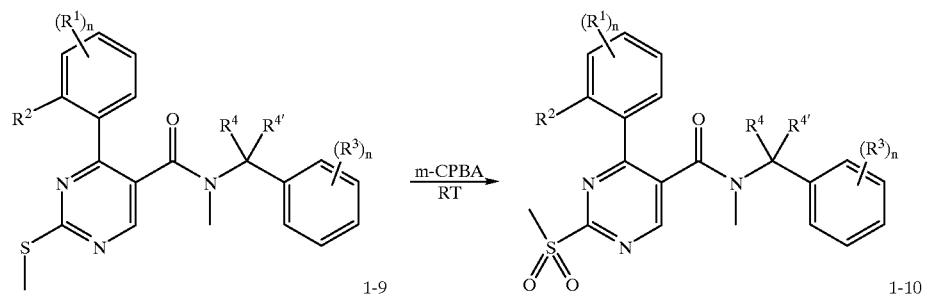

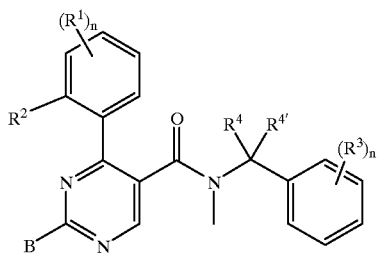
1-11
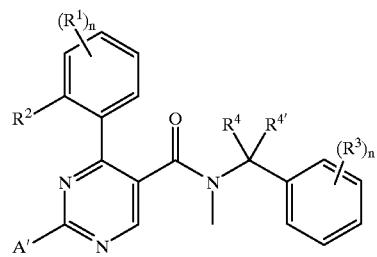
1-12
This reaction type is described in Bioorg. & Med. Chem., Vol.5 No 2, pp437–444, 1997.
$R^1$–$R^4$ and n have the significances given above, B is lower alkoxy, —O—$(CH_2)_{n+1}N(R^4)_2$, —O—$(CH_2)_{n+1}$-morpholinyl or —O—$(CH_2)_{n+1}$-piperidinyl and A' is an amine group such as —$N(R^4)_2$ or piperazinyl which is optionally substituted by morpholinyl, piperidinyl, imidazolyl, benzylamine or —NH—$(CH_2)_{n+1}N(R^4)_2$.
Scheme 6
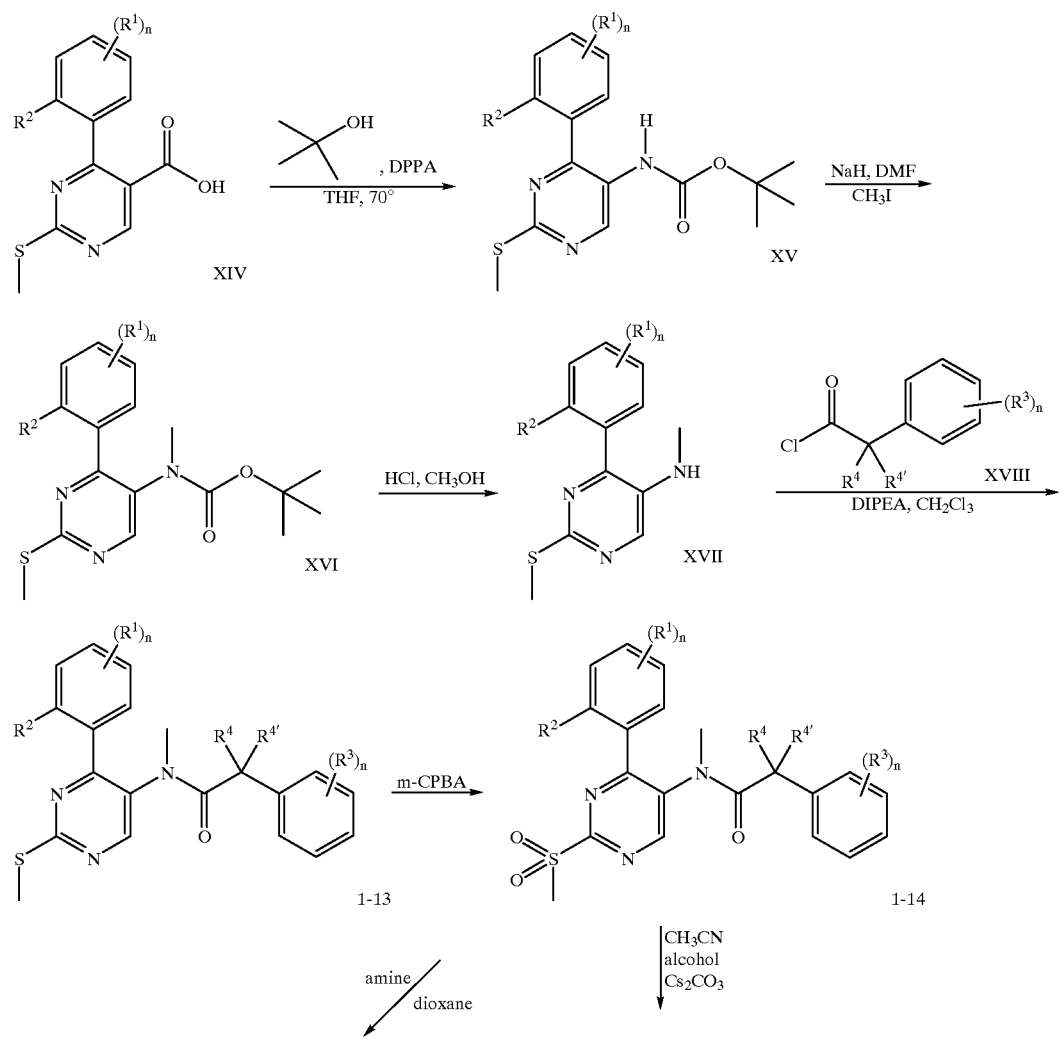

-continued

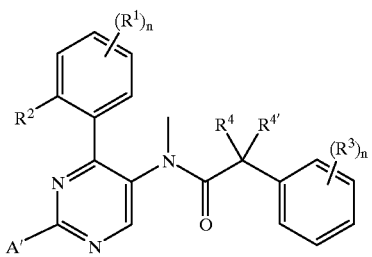

1-15

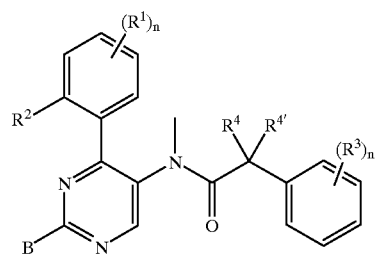

1-16

$R^1$–$R^4$ and n have the significances given above, B is lower alkoxy, —O—$(CH_2)_{n+1}N(R^4)_2$, —O—$(CH_2)_{n+1}$-morpholinyl or —O—$(CH_2)_{n+1}$-piperidinyl and A' is an amine group such as —$N(R^4)_2$ or piperazinyl optionally substituted by morpholinyl, piperidinyl, imidazolyl, benzylamine or —NH—$(CH_2)_{n+1}N(R^4)_2$.

As mentioned earlier, the compounds of formula I and their pharmaceutically usable addition salts possess valuable pharmacological properties. It has been found that the compounds of the present invention are antagonists of the Neurokinin 1 (NK-1, substance P) receptor.

The compounds were investigated in accordance with the tests given hereinafter.

The affinity of test compounds for the $NK_1$ receptor was evaluated at human $NK_1$ receptors in CHO cells infected with the human $NK_1$ receptor (using the Semliki virus expression system) and radiolabelled with [$^3$H]substance P (final concentration 0.6 nM). Binding assays were performed in HEPES buffer (50 mM, pH 7.4) containing BSA (0.04 %) leupeptin (8 μg/ml), $MnCl_2$ (3 mM) and phosphoramidon (2 μM). Binding assays consisted of 250 μl of membrane suspension (1.25×10$^5$ cells/assay tube), 0.125 μl of buffer of displacing agent and 125 μl of [$^3$H]substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 2×2 ml washed of HEPES buffer (50 mM, pH 7.4). The radioactivity retained on the filters was measured by scintillation counting. All assays were performed in triplicate in at least 2 separate experiments.

The affinity to the NK-1 receptor, given as pKi, is in the scope of 8.00–9.20 for the preferred compounds. Examples of such compounds are

| | |
|---|---|
| 4-(2-Chloro-phenyl)-2-(2-dimethylamino-ethoxy)-pyrimidine-5-carboxylic acid(3,5-bis-trifluoromethyl-benzyl)-methyl-amide | 8.45 |
| 4-(2-Chloro-phenyl)-2-(3-dimethylamino-ethoxy)-pyrimidine-5-carboxylic acid(3,5-bis-trifluoromethyl-benzyl)-methyl-amide | 8.11 |
| 4-(2-Chloro-phenyl)-2-(3-dimethylamino-propoxy)-pyrimidine-5-carboxylic acid(3,5-bis-trifluoromethyl-benzyl)-methyl-amide | 8.76 |
| 4-(4-Fluor-2-methyl-phenyl)-2-piperazin-1-yl-pyrimidine-5-carboxylic acid(3,5-bis-trifluoromethyl-benzyl)-methyl-amide | 9.14 |
| 2-(4-Methyl-piperazin-1-yl)-4-naphthalen-1-yl-pyrimidine-5-carboxylic acid(3,5-bis-trifluoromethyl-benzyl)-methyl-amide | 8.54 |

The compounds of formula I as well as their pharmaceutically usable acid addition salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragees and hard gelatine capsules. Lactose, corn starch or derivatives thereof, talc, stearic acid or its salts etc can be used as such excipients e.g. for tablets, dragées and hard gelatine capsules.

Suitable excipients for soft gelatine capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of formula I should be appropriate, although the above upper limit can also be exceeded when necessary. Preferred are dosages of 20 to 500 mg per day. Further preferred are dosages of 50 mg to 200 mg per day.

The following Examples illustrate the present invention without limiting it. All temperatures are given in degrees Celsius.

EXAMPLE 1

2-Methyl-4-phenyl-pyrimidine-5-carboxylic Acid (3,5-bis-trifluoromethyl-benzyl)-methyl-amide a) 2-Methyl-4-phenyl-pyrimidine-5-carboxylic Acid 3,5-bis-trifluoromethyl-benzylamide To a solution of 0.50 g (2.33 mmol) 2-methyl-4-phenyl-pyrimidine-5-carboxylic acid 0.65 ml (4.47 mmol) triethylamin, 0.44 g (2.33 mmol) 1-hydroxy-benzotriazol and 0.44 g (2.33 mmol) N-(3-dimethylaminopropyl)-N'-ethylcarbodiimide hydrochloride in 40 ml $CH_2Cl_2$ 0.68 g (2.8 mmol) 3,5-bis-trifluormethyl-benzylamin were added. The reaction mixture was stirred for 16 hrs. The reaction mixture was diluted with 20 ml $CH_2Cl_2$, washed with 50 ml 0.5N HCl and 50 ml $H_2O$. The aqueous layers were backextracted with 50 ml CH$_2$Cl$_2$. The combined organic layers were dried (MgSO$_4$), filtered and evaporated. The residue was purified by chromatography (SiO$_2$, ethyl acetate) to give 0.80 g (78%) 2-methyl-4-phenyl-pyrimidine-5-carboxylic acid 3,5-bis-trifluoromethyl-benzylamide as a colorless solid, m.p. 188.5–189.5°.

b) 2-Methyl-4-phenyl-pyrimidine-5-carboxylic Acid (3,5-bis-trifluoromethyl-benzyl)-methyl-amide To a solution of 0.67 g (1.52 mmol) methyl-4-phenyl-pyrimidine-5-carboxylic acid 3,5-bis-trifluoromethyl-benzylamide in 10 ml N,N-dimethylformamide 0.08 g (1.98 mmol) sodiumhydride (60% dispersion in mineral oil) was added and the reaction mixture stirred for 1 hr. After the addition of 0.15 ml (2.4 mmol) methyl iodide at 0°, the reaction mixture was stirred for 3 hrs. at RT. The reaction mixture was distributed between 50 ml H$_2$O, 50 ml brine and 50 ml CH$_2$Cl$_2$. The phases were separated, the aqueous layer washed twice with 50 ml CH$_2$Cl$_2$. The combined organic layers were dried (MgSO$_4$), filtered and evaporated. The residue was purified by chromatography (SiO$_2$, ethyl acetate/hexane 4:1) to give 0.50 g (72%) 2-methyl-4-phenyl-pyrimidine-5-carboxylic acid (3,5-bis-trifluoromethyl-benzyl)-methyl-amide as a colorless oil, MS (EI): 453 (M$^+$).

EXAMPLE 2

2-Methyl-4-phenyl-pyrimidine-5-carboxylic Acid (3,5-dichloro-benzyl)-methyl-amide In an analogous manner to that described in Example 1a) there was obtained from 2-methyl-4-phenyl-pyrimidine-5-carboxylic acid and 3,5-dichlorobenzylamine 2-methyl-4-phenyl-pyrimidine-5-carboxylic acid 3,5-dichloro-benzylamide as a colorless solid, m.p. 194–195°, which was methylated as described in Example 1b) to give 2-methyl-4-phenyl-pyrimidine-5-carboxylic acid (3,5-dichloro-benzyl)-methyl-amide as a colorless oil, MS (EI): 385 (M$^+$).

EXAMPLE 3

4-(2-Bromo-phenyl)-2-methyl-pyrimidine-5-carboxylic Acid (3,5-bis-trifluoromethyl-benzyl)-methyl-amide a) 2-(2-Bromo-benzoyl)-3-dimethylamino-acrylic Acid Ethyl Ester To a solution of 25.9 g (95.5 mmol) 3-(2-bromo-phenyl)-3-oxo-propionic acid ethyl ester in 200 ml toluene 18.21 g (152 mmol) N,N-dimethylformamide-dimethylacetal dissolved in 100 ml toluene was added during 1 hr. The reaction mixture was stirred for 1.5 hrs. at 100°. The solvent was evaporated and the residue purified by chromatography (SiO$_2$, CH$_2$Cl$_2$/MeOH 40:1) to give 25 g (80%) 2-(2-bromo-benzoyl)-3-dimethylamino-acrylic acid ethyl ester as a pale brown solid.

b) 4-(2-Bromo-phenyl)-2-methyl-pyrimidine-5-carboxylic Acid Ethyl Ester

To a fresh prepared solution of sodiumethanolate (prepared from 0.77 g (33.7 mmol) Na in 100 ml Ethanol) 3.18 g (33.7 mmol) acetamidinhydrochloride was added. After 10 Min. a solution of 10.0 g (30.6 mmol) 2-(2-bromo-benzoyl)-3-dimethylamino-acrylic acid ethyl ester in 120 ml ethanol was added and the reaction mixture heated for 16 hrs. at 80°. The solvent was evaporated, the residue distributed between 100 ml H$_2$O and 100 ml CH$_2$Cl$_2$. The aqueous phase was extracted twice with 100 ml CH$_2$Cl$_2$. The combined organic layers were dried (MgSO$_4$), filtrated and evaporated. The residue was purified by chromatography (SiO$_2$, CH$_2$Cl$_2$/MeOH 40:1) to give 8.3 g (84%) 4-(2-bromo-phenyl)-2-methyl-pyrimidine-5-carboxylic acid ethyl ester as a pale brown oil.

c) 4-(2-Bromo-phenyl)-2-methyl-pyrimidine-5-carboxylic Acid

To a solution of 8.3 g (25.8 mmol) 4-(2-bromo-phenyl)-2-methyl-pyrimidine-5-carboxylic acid ethyl ester in 10 ml ethanol 1.55 g (38.6 mmol) NaOH in 20 ml H$_2$O was added. After stirring for 1 hr., the reaction mixture was washed with 100 ml diethylether. The pH of the aqueous phase was adjusted to 1 with 25% HCl and than extracted twice with 200 ml CH$_2$Cl$_2$. The combined organic layers were dried (MgSO$_4$), filtrated and evaporated to give 7.0 g (92%) 4-(2-bromo-phenyl)-2-methyl-pyrimidine-5-carboxylic acid as a pale yellow foam.

d) 4-(2-Bromo-Phenyl)-2-methyl-pyrimidine-5-carboxylic Acid (3,5-bis-trifluoromethyl-benzyl)-methyl-amide To a solution of 0.5 g (1.71 mmol) 4-(2-bromo-phenyl)-2-methyl-pyrimidine-5-carboxylic acid, 0.47 ml (3.41 mmol) triethylamin, 0.26 g (1.71 mmol) 1-hydroxybenzotriazol and 0.32 g (1.71 mmol) N-(3-dimethylaminopropyl)-N'-ethylcarbodiimide hydrochloride in 40 ml CH$_2$Cl$_2$ 0.52 g (2.0 mmol) (3,5-bis-trifluoromethyl-benzyl)-methyl-amine were added. The reaction mixture was stirred for 16 hrs. The reaction mixture was diluted with 20 ml CH$_2$Cl$_2$, washed with 50 ml 0.5N HCl and 50 ml H$_2$O. The aqueous layers were backextracted with 50 ml CH$_2$Cl$_2$. The combined organic layers were dried (MgSO$_4$), filtered and evaporated. The residue was purified by chromatography (SiO$_2$, ethyl acetate) to give 0.7 g (77%) 4-(2-bromo-phenyl)-2-methyl-pyrimidine-5-carboxylic acid (3,5-bis-trifluoromethyl-benzyl)-methyl-amide as a colorless solid, m.p. 121.5–122.5°.

EXAMPLE 4

4-(2-Bromo-phenyl)-2-methyl-pyrimidine-5-carboxylic Acid 3,5-bis-trifluoromethyl-benzylamide To a solution of 0.5 g (1.71 mmol) 4-(2-bromo-phenyl)-2-methyl-pyrimidine-5-carboxylic acid, 0.47 ml (3.41 mmol) triethylamin, 0.26 g (1.71 mmol) 1-hydroxybenzotriazol and 0.32 g (1.71 mmol) N-(3-dimethylaminopropyl)-N'-ethylcarbodiimide hydrochloride in 40 ml CH$_2$Cl$_2$ 0.49 g (2.05 mmol) 3.5-bis-trifluormethylbenzylamin was added. The reaction mixture was stirred for 16 hrs. The reaction mixture was diluted with 20 ml CH$_2$Cl$_2$, washed with 50 ml 0.5N HCl and 50 ml H$_2$O. The aqueous layers were backextracted with 50 ml CH$_2$Cl$_2$. The combined organic layers were dried (MgSO$_4$), filtered and evaporated. The residue was purified by chromatography (SiO$_2$, CH$_2$Cl$_2$/MeOH) to give 0.4 g (45 %) 4-(2-bromo-phenyl)-2-methyl-pyrimidine-5-carboxylic acid 3,5-bis-trifluoromethyl-benzylamide as a colorless solid, m.p. 137.5–138.5°.

EXAMPLE 5

2,4-Diphenyl-pyrimidine-5-carboxylic Acid (3,5-bis-trifluormethyl-benzyl)-methyl-amide In an analogous manner to that described in Example 1a) there was obtained from 2,4-diphenyl-pyrimidine-5-carboxylic acid and 3,5-bis-trifluoromethyl-benzylamine 2,4-diphenyl-pyrimidine-5-carboxylic acid 3,5-bis-trifluoromethyl-benzylamide as a colorless solid, m.p.>220°, which was methylated as described in Example 1b) to give 2,4-diphenyl-pyrimidine-5-carboxylic acid (3,5-bis-trifluormethyl-benzyl)-methyl-amide as a colorless oil, MS (ISP): 516.2 (M+H$^+$).

EXAMPLE 6

2,4-Diphenyl-pyrimidine-5-carboxylic Acid (3,5-dichlorobenzyl)-methyl-amide

In an analogous manner to that described in Example 1a) there was obtained from 2,4-diphenyl-pyrimidine-5-carboxylic acid and 3,5-dichlor-benzylamine 2,4-diphenyl-pyrimidine-5-carboxylic acid 3,5-bis-chloro-benzylamide as a colorless solid, m.p.>220°, which was methylated as described in Example 1b) to give 2,4-diphenyl-pyrimidine-5-carboxylic acid (3,5-dichlorobenzyl)-methyl-amide as a colorless oil, MS (ISP): 448 (M+H+).

EXAMPLE 7

4-Phenyl-2-propyl-pyrimidine-5-carboxylic Acid (3,5-dichloro-benzyl)-methyl-amide In an analogous manner to that described in Example 1a) there was obtained from 4-phenyl-2-propyl-pyrimidine-5-carboxylic acid and 3,5-dichlorobenzylamine 4-phenyl-2-propyl-pyrimidine-5-carboxylic acid 3,5-dichloro-benzylamide as a colorless solid, m.p. 183°, which was methylated as described in Example 1b) to give 4-phenyl-2-propyl-pyrimidine-5-carboxylic acid (3,5-dichloro-benzyl)-methyl-amide as a colorless oil, MS (EI): 413 (M+).

The 4-phenyl-2-propyl-pyrimidine-5-carboxylic acid used as the starting substance was obtained as follows:

In an analogous manner to that described in example 3b) starting from 2-benzoyl-3-dimethylamino-acrylic acid ethyl ester and butyramidine hydrochloride, followed by saponification as described in example 3c) there was obtained 4-phenyl-2-propyl-pyrimidine-5-carboxylic acid.

EXAMPLE 8

4-Phenyl-2-propyl-pyrimidine-5-carboxylic Acid (3,5-bis-trifluoromethyl-benzyl)-methyl-amide In an analogous manner to that described in Example 1a) there was obtained from 4-phenyl-2-propyl-pyrimidine-5-carboxylic acid and 3,5-bis-trifluoromethyl-benzylamine 4-phenyl-2-propyl-pyrimidine-5-carboxylic acid 3,5-bis-trifluoromethyl-benzylamide as lo a colorless solid, m.p. 194°–195°, which was methylated as described in Example 1 b) to give 4-phenyl-2-propyl-pyrimidine-5-carboxylic acid (3,5-bis-trifluoromethyl-benzyl)-methyl-amide as a colorless oil, MS (ISP): 482.3 (M+H+).

EXAMPLE 9

4-Phenyl-2-pyridin-4-yl-pyrimidine-5-carboxylic Acid (3,5-bis-trifluoromethyl-benzyl)-methyl-amide In an analogous manner to that described in Example 3d) there was obtained from 4-phenyl-2-pyridin-4-yl-pyrimidine-5-carboxylic acid and (3,5-bis-trifluoromethyl-benzyl)-methyl-amine 4-phenyl-2-pyridin-4-yl-pyrimidine-5-carboxylic acid (3,5-bis-trifluoromethyl-benzyl)-methyl-amide as a colorless solid, m.p. 143°–144°.

The 4-phenyl-2-pyridin-4-yl-pyrimidine-5-carboxylic acid used as the starting substance was obtained as follows:

In an analogous manner to that described in example 3b) starting from 2-benzoyl-3-dimethylamino-acrylic acid ethyl ester and isonicotinamidine hydrochloride, followed by saponification as described in example 3c) there was obtained 4-phenyl-2-pyridin-4-yl-pyrimidine-5-carboxylic acid.

EXAMPLE 10

4-Phenyl-[2,2']bipyrimidinyl-5-carboxylic Acid (3,5-bis-trifluoromethyl-benzyl)-methyl-amide In an analogous manner to that described in Example 3d) there was obtained from 4-phenyl-[2,2']bipyrimidinyl-5-carboxylic acid and (3,5-bis-trifluoromethyl-benzyl)-methyl-amine 4-phenyl-[2,2']bipyrimidinyl-5-carboxylic acid (3,5-bis-trifluoromethyl-benzyl)-methyl-amide as a colorless solid, m.p. 172°–173°.

The 4-phenyl-[2,2°]bipyrimidinyl-5-carboxylic acid used as the starting substance was obtained as follows:

In an analogous manner to that described in example 3b) starting from 2-benzoyl-3-dimethylamino-acrylic acid ethyl ester and pyrimidine-2-carboxamidine hydrochloride, followed by saponification as described in example 3c) there was obtained 4-phenyl-[2,2']bipyrimidinyl-5-carboxylic acid.

EXAMPLE 11

2-Methyl-4-naphthalen-1-yl-pyrimidine-5-carboxylic Acid 3,5-bis-trifluoromethyl-benzylamide In an analogous manner to that described in Example 1a) there was obtained from 2-methyl-4-naphthalen-1-yl-pyrimidine-5-carboxylic acid and 3,5-bis-(trifluoromethyl)-benzylamine 2-methyl-4-naphthalen-1-yl-pyrimidine-5-carboxylic acid 3,5-bis-trifluoromethyl-benzylamide as a colorless solid, m.p. 146.7°–146.9°.

The used $^2$-methyl-4-naphthalen-1-yl-pyrimidine-5-carboxylic acid as the starting substance was obtained as follows:

In an analogous manner to that described in example 3a)–3c) starting from 3-naphthalen-1-yl-3-oxo-propionic acid ethyl ester and N,N-dimethylformamide-dimethylacetal there was obtained 2-methyl-4-naphthalen-1-yl-pyrimidine-5-carboxylic acid.

EXAMPLE 12

2-Methyl-4-naphthalen-1-yl-pyrimidine-5-carboxylic Acid (3,5-bis-trifluoromethyl-benzyl)-methyl-amide In an analogous manner to that described in Example 1b) there was obtained from 2-methyl-4-naphthalen-1-yl-pyrimidine-5-carboxylic acid 3,5-bis-trifluoromethyl-benzylamide and methyliodid 2-methyl-4-naphthalen-1-yl-pyrimidine-5-carboxylic acid (3,5-bis-trifluoromethyl-benzyl)-methyl-amide as a colorless solid, m.p. 164.9°–165.2°.

EXAMPLE 13

4-(2-Methoxy-phenyl)-2-methyl-pyrimidine-5-carboxylic Acid (3,5-bis-trifluoromethyl-benzyl)-methyl-amide In an analogous manner to that described in Example 3d) there was obtained from 4-(2-methoxy-phenyl)-2-methyl-pyrimidine-5-carboxylic acid and (3,5-bis-trifluoromethyl-benzyl)-methyl-amine 4-(2-methoxy-phenyl)-2-methyl-pyrimidine-5-carboxylic acid (3,5-bis-trifluoromethyl-benzyl)-methyl-amide as a colorless solid, m.p. 140°–141°.

The used 4-(2-methoxy-phenyl)-2-methyl-pyrimidine-5-carboxylic acid as the starting substance was obtained as follows:

In an analogous manner to that described in example 3a)–3c) starting from 3-(2-methoxy-phenyl)-3-oxopropionic acid ethyl ester and N,N-dimethylformamide-dimethylacetal there was obtained 4-(2-methoxy-phenyl)-2-methyl-pyrimidine-5-carboxylic acid.

EXAMPLE 14

2-Methylsulfanyl-4-phenyl-pyrimidine-5-carboxylic Acid (3,5-bis-trifluoromethyl-benzyl)-methyl-amide To a solution of 3 g (12.18 mmol) 2-methylsulfanyl-4-phenyl-pyrimidine-5-carboxylic acid, 3.32 ml (24.36 mmol) triethylamin, 1.84 g (12.18 mmol) 1-hydroxybenzotriazol and 2.33 g (12.81 mmol) N-(3-dimethylaminopropyl)-N'-ethylcarbodiimide hydrochloride in 170 ml $CH_2Cl_2$ 3.76 g (14.62 mmol) (3,5-bis-trifluoromethyl-benzyl)-methyl-amine were added. The reaction mixture was stirred for 16 hrs. The reaction mixture was diluted with 100 ml $CH_2Cl_2$, washed with 100 ml 0.5N HCl and 100 ml $H_2O$. The aqueous layers were backextracted with 100 ml $CH_2Cl_2$. The combined organic layers were dried ($MgSO_4$), filtered and evaporated. The residue was purified by chromatography ($SiO_2$, $CH_2Cl_2$/ethyl acetate) to give 4.15 g (67%) 2-methylsulfanyl-4-phenyl-pyrimidine-5-carboxylic acid (3,5-bis-trifluoromethyl-benzyl)-methyl-amide as a colorless solid, m.p. 119.1–119.8°.

EXAMPLE 15

2-Methylsulfonyl-4-phenyl-pyrimidine-5-carboxylic Acid (3,5-bis-trifluoromethyl-benzyl)-methyl-amide To a solution of 4.15 g (85.5 mmol) 2-methylsulfanyl-4-phenyl-pyrimidine-5-carboxylic acid (3,5-bis-trifluoromethyl-benzyl)-methyl-amide in 170 ml $CH_2Cl_2$ 5.27 g (21.4 mmol) 3-chloroperbenzoic acid (70%) was added at 50 and the reaction mixture stirred for 3 hrs. at RT. After addition of 150 ml sat. $NaHCO_3$-solution, the layers were separated, the organic phase washed with sat. $NaHCO_3$-solution, dried ($Na_2SO_4$), filtered and evaporated. The residue was purified by chromatography ($SiO_2$, $CH_2Cl_2$/methanol 40:1) to give 4.20 g (95%) 2-methylsulfonyl-4-phenyl-pyrimidine-5-carboxylic acid (3,5-bis-trifluoromethyl-benzyl)-methyl-amide as a colorless solid, MS (EI): 517 ($M^+$).

EXAMPLE 16

2-(4-Methyl-piperazin-1-yl)-4-phenyl-pyrimidine-5-carboxylic Acid (3,5-bis-trifluoromethyl-benzyl)-methyl-amide To a solution of 0.5 g (0.97 mmol) 2-methylsulfonyl-4-phenyl-pyrimidine-5-carboxylic acid (3,5-bis-trifluoromethyl-benzyl)-methyl-amide in 10 ml dioxan 0.27 ml (2.42 mmol) 1-methylpiperazine was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/methanol 9:1) to give 0.4 g (77%) 2-(4-methyl-piperazin-1-yl)-4-phenyl-pyrimidine-5-carboxylic acid (3,5-bis-trifluoromethyl-benzyl)-methyl-amide as a colorless oil, MS (ISP): 538.3 ($M+H^+$).

EXAMPLE 17

2-Benzylamino-4-phenyl-pyrimidine-5-carboxylic Acid (3,5-bis-trifluoromethyl-benzyl)-methyl-amide To a solution of 0.4 g (0.77 mmol) 2-methylsulfonyl-4-phenyl-pyrimidine-5-carboxylic acid (3,5-bis-trifluoromethyl-benzyl)-methyl-amide in 10 ml dioxan 0.21 ml (1.923 mmol) benzylamin were added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/methanol 40:1) to give 0.2 g (47%) 2-benzylamino-4-phenyl-pyrimidine-5-carboxylic acid (3,5-bis-trifluoromethyl-benzyl)-methyl-amide as a colorless solid, 117.2–118.1°.

EXAMPLE 18

2-Morpholin-4-yl-4-phenyl-pyrimidine-5-carboxylic Acid (3,5-bis-trifluoromethyl-benzyl)-methyl-amide To a solution of 0.4 g (0.77 mmol) 2-methylsulfonyl-4-phenyl-pyrimidine-5-carboxylic acid (3,5-bis-trifluoromethyl-benzyl)-methyl-amide in 10 ml dioxan 0.17 ml (1.93 mmol) morpholin was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/methanol 40:1) to give 0.21 g (52%) 2-morpholin-4-yl-4-phenyl-pyrimidine-5-carboxylic acid (3,5-bis-trifluoromethyl-benzyl)-methyl-amide as a colorless solid, 168.1–168.4°.

EXAMPLE 19

4-Phenyl-2-piperazin-1-yl-pyrimidine-5-carboxylic Acid (3,5-bis-trifluoromethyl-benzyl)-methyl-amide To a solution of 0.5 g (0.96 mmol) 2-methylsulfonyl-4-phenyl-pyrimidine-5-carboxylic acid (3,5-bis-trifluoromethyl-benzyl)-methyl-amide in 10 ml dioxan 0.208 g (2.15 mmol) piperazin was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/methanol 40:1) to give 0.42 g (83%) 4-phenyl-2-piperazin-1-yl-pyrimidine-5-carboxylic acid (3,5-bis-trifluoromethyl-benzyl)-methyl-amide as a colorless oil, MS (ISP): 524.1 ($M+H^+$).

EXAMPLE 20

(3R,5S)-2-(3,5-Dimethyl-piperazin-1-yl)-4-phenyl-pyrimidine-5-carboxylic Acid (3,5-bis-trifluoromethyl-benzyl)-methyl-amide To a solution of 0.5 g (0.96 mmol) 2-methylsulfonyl-4-phenyl-pyrimidine-5-carboxylic acid (3,5-bis-trifluoromethyl-benzyl)-methyl-amide in 10 ml dioxan 0.276 g (2.15 mmol) cis-2,6-dimethyl-piperazin was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/methanol 40:1) to give 0.51 g (96%) (3R,5S)-2-(3,5-dimethyl-piperazin-1-yl)-4-phenyl-pyrimidine-5-carboxylic acid (3,5-bis-trifluoromethyl-benzyl)-methyl-amide as a colorless oil, MS (ISP): 552.1 ($M+H^+$).

EXAMPLE 21

2-(2-Dimethylamino-ethylamino)-4-phenyl-pyrimidine-5-carboxylic Acid (3,5-bis-trifluoromethyl-benzyl)-methyl-amide To a solution of 0.4 g (0.77 mmol) 2-methylsulfonyl-4-phenyl-pyrimidine-5-carboxylic acid (3,5-bis-trifluoromethyl-benzyl)-methyl-amide in 10 ml dioxan 0.211 ml (1.93 mmol) 2-dimethylaminoethylamin was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/methanol/$NH_4OH$ 140:10:1) to give 0.22 g (54%) 2-(2-dimethylamino-ethylamino)-4-phenyl-pyrimidine-5-carboxylic acid (3,5-bis-trifluoromethyl-benzyl)-methyl-amide as a colorless solid, m.p. 109.5–110.3°.

EXAMPLE 22

4-Phenyl-2-piperidin-1-yl-pyrimidine-5-carboxylic Acid (3,5-bis-trifluoromethyl-benzyl)-methyl-amide To a solution of 0.5 g (0.96 mmol) 2-methylsulfonyl-4-phenyl-pyrimidine-5-carboxylic acid (3,5-bis-trifluoromethyl-benzyl)-methyl-amide in 10 ml dioxan 0.183 g (2.15 mmol) piperidin was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/ethyl acetate 20:1) to give 0.48 g (95%) 4-phenyl-2-piperidin-1-yl-pyrimidine-5-carboxylic acid (3,5-bis-trifluoromethyl-benzyl)-methyl-amide as a waxy pale yellow solid, MS (ISP): 523.2 (M+H$^+$).

EXAMPLE 23

2-[4-(2-Hydroxy-ethyl)-piperazin-1-yl]-4-phenyl-pyrimidine-5-carboxylic Acid (3,5-bis-trifluoromethyl-benzyl)-methyl-amide To a solution of 0.5 g (0.96 mmol) 2-methylsulfonyl-4-phenyl-pyrimidine-5-carboxylic acid (3,5-bis-trifluoromethyl-benzyl)-methyl-amide in 10 ml dioxan 0.28 g (2.15 mmol) N-(2-hydroxyethyl)piperazin was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH 6:1) to give 0.43 g (78%) 2-[4-(2-hydroxy-ethyl)-piperazin-1-yl]-4-phenyl-pyrimidine-5-carboxylic acid (3,5-bis-trifluoromethyl-benzyl)-methyl-amide as a waxy pale yellow solid, MS (ISP): 568.2 (M+H$^+$).

EXAMPLE 24

2-(2-Morpholin-4-yl-ethoxy)-4-phenyl-pyrimidine-5-carboxylic Acid (3,5-bis-trifiluoromethyl-benzyl)-methyl-amide To a solution of 0.5 g (0.96 mmol) 2-methylsulfonyl-4-phenyl-pyrimidine-5-carboxylic acid (3,5-bis-trifluoromethyl-benzyl)-methyl-amide in 20 ml acetonitrile 0.15 g (1.16 mmol) N-(2-hydroxyethyl)morpholine and 1.57 g (4.83 mmol) $Cs_2CO_3$ were added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH 40:1) to give 0.39 g (68%) 2-(2-morpholin-4-yl-ethoxy)-4-phenyl-pyrimidine-5-carboxylic acid (3,5-bis-trifluoromethyl-benzyl)-methyl-amide as a pale yellow oil, MS (ISP): 569.2 (M+H$^+$).

EXAMPLE 25

4-Phenyl-2-(2-piperidin-1-yl-ethoxy)-pyrimidine-5-carboxylic Acid (3,5-bis-trifluoromethyl-benzyl)-methyl-amide To a solution of 0.5 g (0.96 mmol) 2-methylsulfonyl-4-phenyl-pyrimidine-5-carboxylic acid (3,5-bis-trifluoromethyl-benzyl)-methyl-amide in 20 ml acetonitrile 0.15 g (1.16 mmol) N-(2-hydroxyethyl)piperidin and 1.57 g (4.83 mmol) $Cs_2CO_3$ were added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH/$NH_4OH$ 200:10:1) to give 0.47 g (85%) 4-phenyl-2-(2-piperidin-1-yl-ethoxy)-pyrimidine-5-carboxylic acid (3,5-bis-trifluoromethyl-benzyl)-methyl-amide as a pale yellow oil, MS (ISP): 567.2 (M+H$^+$).

EXAMPLE 26

2-(2-Dimethylamino-ethoxy)-4-phenyl-pyrimidine-5-carboxylic Acid (3,5-bis-trifluoromethyl-benzyl)-methyl-amide To a solution of 0.5 g (0.96 mmol) 2-methylsulfonyl-4-phenyl-pyrimidine-5-carboxylic acid (3,5-bis-trifluoromethyl-benzyl)-methyl-amide in 20 ml acetonitrile 0.10 g (1.16 mmol) 2-dimethylamino-ethanol and 1.57 g (4.83 mmol) $Cs_2CO_3$ were added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH/$NH_4OH$ 110:10:1) to give 0.43 g (82%) 2-(2-dimethylamino-ethoxy)-4-phenyl-pyrimidine-5-carboxylic acid (3,5-bis-trifluoromethyl-benzyl)-methyl-amide as a pale yellow oil, MS (ISP): 527.2 (M+H$^+$).

EXAMPLE 27

2-(3-Dimethylamino-propoxy)-4-phenyl-pyrimidine-5-carboxylic Acid (3,5-bis-trifluoromethyl-benzyl)-methyl-amide To a solution of 0.5 g (0.96 mmol) 2-methylsulfonyl-4-phenyl-pyrimidine-5-carboxylic acid (3,5-bis-trifluoromethyl-benzyl)-methyl-amide in 20 ml acetonitrile 0.14 ml (1.16 mmol) 2-dimethylamino-propanol and 1.57 g (4.83 mmol) $Cs_2CO_3$ were added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography (SiO$_2$, CH$_2$Cl$_2$/MeOH/NH$_4$OH 110:10:1) to give 0.50 g (95%) 2-(3-dimethylamino-propoxy)-4-phenyl-pyrimidine-5-carboxylic acid (3,5-bis-trifluoromethyl-benzyl)-methyl-amide as a pale yellow oil, MS (ISP): 541.2 (M+H$^+$).

EXAMPLE 28

2-Methoxy-4-phenyl-pyrimidine-5-carboxylic Acid (3,5-bis-trifluoromethyl-benzyl)-methyl-amide To a suspension of of 0.4 g (0.77 mmol) 2-methylsulfonyl-4-phenyl-pyrimidine-5-carboxylic acid (3,5-bis-trifluoromethyl-benzyl)-methyl-amide in 10 ml methanol 0.10 g (1.93 mmol) sodiummethanolat (95%) was added. The reaction mixture was stirred for 16 hrs. After evaporation of the solvent, the residue was distributed between 50 ml CH$_2$Cl$_2$ and 50 ml H$_2$O. The aqueous layer was extracted with 50 ml CH$_2$Cl$_2$, the combined organic layers dried (MgSO$_4$), filtered and evaporated. The residue was purified by chromatography (SiO$_2$, CH$_2$Cl$_2$/MeOH 40:1) to give 0.23 g (63%) 2-methoxy-4-phenyl-pyrimidine-5-carboxylic acid (3,5-bis-trifluoromethyl-benzyl)-methyl-amide as a colorless solid, m.p. 101.2–102°.

EXAMPLE 29

2-Carbamoylmethyl-4-phenyl-pyrimidine-5-carboxylic Acid (3,5-bis-trifluoromethyl-benzyl)-methyl-amide In an analogous manner to that described in Example 3d) there was obtained from 2-carbamoylmethyl-4-phenyl-pyrimidine-5-carboxylic acid and (3,5-bis-trifluoromethyl-benzyl)-methyl-amine 2-carbamoylmethyl-4-phenyl-pyrimidine-5-carboxylic acid (3,5-bis-trifluoromethyl-benzyl)-methyl-amide as a colorless solid, m.p. 161°–163°.

The 2-carbamoylmethyl-4-phenyl-pyrimidine-5-carboxylic acid used as the starting substance was obtained as follows:

In an analogous manner to that described in example 3b) starting from 2-benzoyl-3-dimethylamino-acrylic acid ethyl ester and malonamidine hydrochloride, followed by saponification as described in Example 3c) there was obtained 2-carbamoylmethyl-4-phenyl-pyrimidine-5-carboxylic acid.

EXAMPLE 30

2-Cyanomethyl-4-phenyl-pyrimidine-5-carboxylic Acid (3,5-bis-trifluoromethyl-benzyl)-methyl-amide To a solution of 0.50 g (1.01 mmol) in 2-carbamoylmethyl-4-phenyl-pyrimidine-5-carboxylic acid (3,5-bis-trifluoromethyl-benzyl)-methyl-amide and 0.17 ml pyridine in 10 ml dioxane 0.15 ml (1.06 mmol) trifluoraceticanhydrid were added and the resulting reaction mixture was stirred for 1 hr. at 50°. The reaction mixture was poured on Ice/H$_2$O and extracted three times with 50 ml CH$_2$Cl$_2$. The combined organic layers were dried (MgSO$_4$), filtered and evaporated. The residue was purified by chromatography (SiO$_2$, CH$_2$Cl$_2$/MeOH 30:1) to give 0.25 g (51%) 2-cyanomethyl-4-phenyl-pyrimidine-5-carboxylic acid (3,5-bis-trifluoromethyl-benzyl)-methyl-amide as a colorless solid, m.p. 114–116°.

EXAMPLE 31

2-Hydroxymethyl-4-phenyl-pyrimidine-5-carboxylic Acid (3,5-bis-trifluoromethyl-benzyl)-methyl-amide In an analogous manner to that described in Example 3d) there was obtained from 2-hydroxymethyl-4-phenyl-pyrimidine-5-carboxylic acid and (3,5-bis-trifluoromethyl-benzyl)-methyl-amine 2-hydroxymethyl-4-phenyl-pyrimidine-5-carboxylic acid (3,5-bis-trifluoromethyl-benzyl)-methyl-amide as a colorless oil, MS (EI): 469 (M$^+$).

The used 2-hydroxymethyl-4-phenyl-pyrimidine-5-carboxylic acid as the starting substance was obtained as follows:

In an analogous manner to that described in example 3b) starting from 2-benzoyl-3-dimethylamino-acrylic acid ethyl ester and 2-hydroxy-acetamidine hydrochloride followed by saponification as described in Example 3c), there was obtained 2-hydroxymethyl-4-phenyl-pyrimidine-5-carboxylic acid.

EXAMPLE 32

2-Dimethylaminomethyl-4-phenyl-pyrimidine-5-carboxylic Acid (3,5-bis-trifluoromethyl-benzyl)-methyl-amide a) Methanesulfonic Acid 5-[(3,5-bis-trifluoromethyl-benzyl)-methyl-carbamoyl]-4-phenyl-pyrimidin-2-ylmethyl Ester To a solution of 2.64 g (5.62 mmol) 2-hydroxymethyl-4-phenyl-pyrimidine-5-carboxylic acid (3,5-bis-trifluoromethyl-benzyl)-methyl-amide and 1.17 ml (8.44 mmol) triethylamine in 30 ml CH$_2$Cl$_2$ 0.479 ml (6.19 mmol) methansulfonylchloride were added at 0°. The reaction mixture was stirred for 16 hrs. The reaction mixture was poured on sat. NaHCO$_3$— solution and extracted three times with 50 ml CH$_2$Cl$_2$. The combined organic layers were dried (MgSO$_4$), filtered and evaporated. The residue was purified by chromatography (SiO$_2$, CH$_2$CL2/ethyl acetate 8:1) to give 2.30 g (74%) methanesulfonic acid 5-[(3,5-bis-trifluoromethyl-benzyl)-methyl-carbamoyl]-4-phenyl-pyrimidin-2-ylmethyl ester as a colorless viscous oil, MS (ISP): 548.1 (M+H$^+$).

b) 2-Dimethylaminomethyl-4-phenyl-pyrimidine-5-carboxylic Acid (3,5-bis-trifluoromethyl-benzyl)-methyl-amide To a solution of 0.40 g (0.73 mmol) methanesulfonic acid 5-[(3,5-bis-trifluoromethyl-benzyl)-methyl-carbamoyl]-4-phenyl-pyrimidin-2-ylmethyl ester in 5 ml CH$_2$Cl$_2$ 1 ml 5.6 m dimethylamin-solution in ethanol were added. The reaction mixture was stirred for 16 hrs. at RT. The reaction mixture was poured into H$_2$O and extracted three times with 50 ml CH$_2$Cl$_2$. The combined organic layers were dried (MgSO$_4$), filtered and evaporated. The residue was purified by chromatography (SiO$_2$, CH$_2$Cl$_2$/MeOH 20:1) to give 0.33 g (90%) 2-dimethylaminomethyl-4-phenyl-pyrimidine-5-carboxylic acid (3,5-bis-trifluoromethyl-benzyl)-methyl-amide as a colorless oil, MS (ISP): 497.2 (M+H$^+$).

EXAMPLE 33

2-Morpholin-4-ylmethyl-4-phenyl-pyrimidine-5-carboxylic Acid (3,5-bis-trifluoromethyl-benzyl)-methyl-amide To a solution of 0.40 g (0.73 mmol) methanesulfonic acid 5-[(3,5-bis-trifluoromethyl-benzyl)-methyl-carbamoyl]-4-phenyl-pyrimidin-2-ylmethyl ester in 5 ml CH$_2$Cl$_2$ 0.095 ml (1.10 mmol) morpholine were added. The reaction mixture was stirred for 16 hrs. at RT. The reaction mixture was poured into H$_2$O and extracted three times with 50 ml CH$_2$Cl$_2$. The combined organic layers were dried (MgSO$_4$), filtered and evaporated. The residue was purified by chromatography (SiO$_2$, CH$_2$Cl$_2$/MeOH 10:1) to give 0.33 g (88%) 2-morpholin-4-ylmethyl-4-phenyl-pyrimidine-5-carboxylic acid (3,5-bis-trifluoromethyl-benzyl)-methyl-amide as a pale yellow waxy solid, MS (ISP): 539.3 (M+H$^+$).

EXAMPLE 34

2-(4-Methyl-piperazin-1-ylmethyl)-4-phenyl-pyrimidine-5-carboxylic Acid (3,5-bis-trifluoromethyl-benzyl)-methyl-amide To a solution of 0.40 g (0.73 mmol) methanesulfonic acid 5-[(3,5-bis-trifluoromethyl-benzyl)-methyl-carbamoyl]-4-phenyl-pyrimidin-2-ylmethyl ester in 5 ml $CH_2Cl_2$ 0.12 ml (1.1 mmol) N-methylpiperazine were added. The reaction mixture was stirred for 16 hrs. at RT and than poured into $H_2O$ and extracted three times with 50 ml $CH_2Cl_2$. The combined organic layers were dried ($MgSO_4$), filtered and evaporated. The residue was purified by chromatography ($SiO_2$, $CH_2Cl_2$/MeOH 10:1) to give 0.31 g (77%) 2-(4-methyl-piperazin-1-ylmethyl)-4-phenyl-pyrimidine-5-carboxylic acid (3,5-bis-trifluoromethyl-benzyl)-methyl-amide as a pale yellow waxy solid, MS (ISP): 552.2 ($M+H^+$).

EXAMPLE 35

4-Phenyl-2-piperidin-1-ylmethyl-pyrimidine-5-carboxylic Acid (3,5-bis-trifluoromethyl-benzyl)-methyl-amide To a solution of 0.40 g (0.73 mmol) methanesulfonic acid 5-[(3,5-bis-trifluoromethyl-benzyl)-methyl-carbamoyl]-4-phenyl-pyrimidin-2-ylmethyl ester in 5 ml $CH_2Cl_2$ added 0.11 ml (1.1 mmol) piperidine were added. The reaction mixture was stirred for 16 hrs. at RT and than poured into $H_2O$ and extracted three times with 50 ml $CH_2Cl_2$. The combined organic layers were dried ($MgSO_4$), filtered and evaporated. The residue was purified by chromatography ($SiO_2$, $CH_2Cl_2$/MeOH 10:1) to give 0.32 g (81%) 4-phenyl-2-piperidin-1-ylmethyl-pyrimidine-5-carboxylic acid (3,5-bis-trifluoromethyl-benzyl)-methyl-amide as a pale yellow waxy solid, MS (ISP): 537.2 ($M+H^+$).

EXAMPLE 36

2-Imidazol-1-ylmethyl-4-phenyl-pyrimidine-5-carboxylic Acid (3,5-bis-trifluoromethyl-benzyl)-methyl-amide To a solution of 0.40 g (0.73 mmol) methanesulfonic acid 5-[(3,5-bis-trifluoromethyl-benzyl)-methyl-carbamoyl]-4-phenyl-pyrimidin-2-ylmethyl ester and 0.04 g (0.80 mmol) sodiummethanolate in 15 ml N,N-dimethylformamide 0.59 g (0.88 mmol) imidazole was added. The reaction mixture was stirred for 16 hrs. at RT. The reaction mixture was evaporated and the residue distributed between $H_2O$ and $CH_2Cl_2$. The aqueous layer was extracted twice with 50 ml $CH_2Cl_2$. The combined organic layers were dried ($MgSO_4$), filtered and evaporated. The residue was purified by chromatography ($SiO_2$, $CH_2Cl_2$/MeOH 10:1) to give 0.24 g (63%) 2-imidazol-1-ylmethyl-4-phenyl-pyrimidine-5-carboxylic acid (3,5-bis-trifluoromethyl-benzyl)-methyl-amide as a pale yellow solid, MS (ISP): 520.2 ($M+H^+$).

EXAMPLE 37

4-(2-Bromo-phenyl)-2-methylsulfanyl-pyrimidine-5-carboxylic Acid (3,5-bis-trifluoromethyl-benzyl)-methyl-amide a) 4-(2-Bromo-phenyl)-2-methylsulfanyl-pyrimidine-5-carboxylic Acid Ethyl Ester To a suspension of 3.81 g (46.54 mmol) sodiumacetate and 6.47 g (23.27 mmol) S-methylisothiourea sulfate in 100 ml N,N-dimethylformamide a solution of 6.90 g (21.15 mmol) 2-(2-bromo-benzoyl)-3-dimethylamino-acrylic acid ethyl ester in 20 ml N,N-dimethylformamide was added at once and the resulting reaction mixture was stirred for 16 hrs. at 90°. The solvent was evaporated and the residue distributed between 100 ml $CH_2Cl_2$ and 100 ml $H_2O$. The aqueous phase was extracted twice with 100 ml $CH_2Cl_2$. The combined organic layers were dried ($MgSO_4$), filtered and evaporated. The residue was purified by chromatography ($SiO_2$, $CH_2Cl_2$) to give 5.20 g (69%) 4-(2-bromo-phenyl)-2-methylsulfanyl-pyrimidine-5-carboxylic acid ethyl ester as a pale green oil.

b) 4-(2-Bromo-phenyl)-2-methylsulfanyl-pyrimidine-5-carboxylic Acid

To a solution of 5.10 g (14.4 mmol) 4-(2-bromo-phenyl)-2-methylsulfanyl-pyrimidine-5-carboxylic acid ethyl ester in 10 ml ethanol 10 ml 2N NaOH-solution were added. After stirring for 1 hr. 50 ml $H_2O$ and 50 ml $CH_2Cl_2$ were added to the yellow solution. The pH of the aqueous phase was adjusted to 1 with 25% HCl the phases separated and the aqueous phase extracted twice with 200 ml $CH_2Cl_2$. The combined organic layers were dried ($MgSO_4$), filtrated and evaporated to give 4.60 g (98%) 4-(2-bromo-phenyl)-2-methylsulfanyl-pyrimidine-5-carboxylic acid as a off-white solid.

c) 4-(2-Bromo-phenyl)-2-methylsulfanyl-pyrimidine-5-carboxylic Acid (3,5-bis-trifluoromethyl-benzyl)-methyl-amide To a solution of 2 g (6.15 mmol) 4-(2-bromo-phenyl)-2-methylsulfanyl-pyrimidine-5-carboxylic acid, 1.71 ml (12.3 mmol) triethylamin, 0.94 g (6.15 mmol) 1-hydroxybenzotriazol and 1.17 g (6.15 mmol) N-(3-dimethylaminopropyl)-N'-ethylcarbodiimide in 70 ml $CH_2Cl_2$ 1.63 g (6.34 mmol) (3,5-bis-trifluoromethyl-benzyl)-methyl-amine were added. The reaction mixture was stirred for 16 hrs. The reaction mixture was diluted with 50 ml $CH_2Cl_2$, washed with 50 ml 0.5N HCl and 50 ml $H_2O$. The aqueous layers were backextracted with 75 ml $CH_2Cl_2$. The combined organic layers were dried ($MgSO_4$), filtered and evaporated. The residue was purified by chromatography ($SiO_2$, $CH_2Cl_2$/MeOH 40:1) to give 3.0 g (86%) 4-(2-bromo-phenyl)-2-methylsulfanyl-pyrimidine-5-carboxylic acid (3,5-bis-trifluoromethyl-benzyl)-methyl-amide as a white foam, MS (ISP): 566, 564 ($M+H^+$).

EXAMPLE 38

4-(2-Bromo-phenyl)-2-methanesulfonyl-pyrimidine-5-carboxylic Acid (3,5-bis-trifluoromethyl-benzyl)-methyl-amide In an analogous manner to that described in Example 15 there was obtained from 4-(2-bromo-phenyl)-2-methylsulfanyl-pyrimidine-5-carboxylic acid (3,5-bis-trifluoromethyl-benzyl)-methyl-amide and 3-chloroperbenzoicacid 4-(2-bromo-phenyl)-2-methanesulfonyl-pyrimidine-5-carboxylic acid (3,5-bis-trifluoromethyl-benzyl)-methyl-amide as a white foam, MS (ISP): 598, 596 ($M+H^+$).

EXAMPLE 39

2-Amino-4-(2-bromo-phenyl)-pyrimidine-5-carboxylic Acid (3,5-bis-trifluoromethyl-benzyl)-methyl-amide To a solution of 0.42 g (0.7 mmol) 4-(2-bromo-phenyl)-2-methylsulfonyl-pyrimidine-5-carboxylic acid (3,5-bis-trifluoromethyl-benzyl)-methyl-amide in 30 ml N,N-dimethylformamide a stream of $NH_3$ was introduced during 10 Min. The reaction solution was stirred for 4 hrs. The solvent was evaporated and the residue distributed between 20 ml $CH_2Cl_2$ and 20 ml $H_2O$. The aqueous phase was extracted twice with 30 ml CH$_2$Cl$_2$. The combined organic layers were dried (MgSO$_4$), filtered and evaporated. The residue was purified by chromatography (SiO$_2$, CH$_2$Cl$_2$/MeOH/NH$_4$OH 140:10:1) to give 0.29 g (77%) 2-amino-4-(2-bromo-phenyl)-pyrimidine-5-carboxylic acid (3,5-bis-trifluoromethyl-benzyl)-methyl-amide as a white foam, MS (ISP): 535.1, 533.1 (M+H$^+$).

EXAMPLE 40

4-(2-Bromo-phenyl)-2-(4-methyl-piperazin-1-yl)-pyrimidine-5-carboxylic Acid (3,5-bis-trifluoromethyl-benzyl)-methyl-amide In an analogous manner to that described in Example 16 there was obtained from 4-(2-bromo-phenyl)-2-methylsulfonyl-pyrimidine-5-carboxylic acid (3,5-bis-trifluoromethyl-benzyl)-methyl-amide and 1-methylpiperazin 4-(2-bromo-phenyl)-2-(4-methyl-piperazin-1-yl)-pyrimidine-5-carboxylic acid (3,5-bis-trifluoromethyl-benzyl)-methyl-amide as a white foam, MS (ISP): 618.1, 616.1 (M+H$^+$), which was treated with fumaric acid in the usual way to give 4-(2-bromo-phenyl)-2-(4-methyl-piperazin-1-yl)-pyrimidine-5-carboxylic acid (3,5-bis-trifluoromethyl-benzyl)-methyl-amide fumarate (1:1), m.p. 179–180°.

EXAMPLE 41

(3R,5S)-4-(2-bromo-phenyl)-2-(3,5-dimethyl-piperazin-1-yl)-pyrimidine-5-carboxylic Acid (3,5-bis-trifluoromethyl-benzyl)-methyl-amide In an analogous manner to that described in Example 20 there was obtained from 4-(2-bromo-phenyl)-2-methylsulfanyl-pyrimidine-5-carboxylic acid (3,5-bis-trifluoromethyl-benzyl)-methyl-amide and cis-2,6-dimethyl-piperazin (3R,5S)-4-(2-bromo-phenyl)-2-(3,5-dimethyl-piperazin-1-yl)-pyrimidine-5-carboxylic acid (3,5-bis-trifluoromethyl-benzyl)-methyl-amide as a white foam, MS (ISP): 632.0, 630.0 (M+H$^+$).

EXAMPLE 42

4-(2-Bromo-phenyl)-2-piperazin-1-yl-pyrimidine-5-carboxylic Acid (3,5-bis-trifluoromethyl-benzyl)-methyl-amide In an analogous manner to that described in Example 19 there was obtained from 4-(2-bromo-phenyl)-2-methylsulfonyl-pyrimidine-5-carboxylic acid (3,5-bis-trifluoromethyl-benzyl)-methyl-amide and Piperazin 4-(2-bromo-phenyl)-2-piperazin-1-yl-pyrimidine-5-carboxylic acid (3,5-bis-trifluoromethyl-benzyl)-methyl-amide as a white foam, MS (ISP): 603.9, 601.9 (M+H$^+$).

EXAMPLE 43

4-(2-Bromo-phenyl)-2-morpholin-4-yl-pyrimidine-5-carboxylic Acid (3,5-bis-trifluoromethyl-benzyl)-methyl-amide In an analogous manner to that described in Example 18 there was obtained from 4-(2-bromo-phenyl)-2-methylsulfonyl-pyrimidine-5-carboxylic acid (3,5-bis-trifluoromethyl-benzyl)-methyl-amide and morpholine 4-(2-bromo-phenyl)-2-morpholin-4-yl-pyrimidine-5-carboxylic acid (3,5-bis-trifluoromethyl-benzyl)-methyl-amide as a white foam, MS (ISP): 605, 603 (M+H$^+$).

EXAMPLE 44

4-(2-Chloro-phenyl)-2-methylsulfanyl-pyrimidine-5-carboxylic Acid (3,5-bis-trifluoromethyl-benzyl)-methyl-amide In an analogous manner to that described in Example 37c) there was obtained from 4-(2-chloro-phenyl)-2-methylsulfanyl-pyrimidine-5-carboxylic acid and (3,5-bis-trifluoromethyl-benzyl)-methyl-amine 4-(2-chloro-phenyl)-2-methylsulfanyl-pyrimidine-5-carboxylic acid (3,5-bis-trifluoromethyl-benzyl)-methyl-amide as a white foam, MS (EI): 519 (M$^+$).

The 4-(2-chloro-phenyl)-2-methylsulfanyl-pyrimidine-5-carboxylic acid used as the starting substance was obtained as follows:

In an analogous manner to that described in Example 37a), b) there was obtained from 2-(2-chloro-benzoyl)-3-dimethylamino-acrylic acid ethyl ester and S-methylisothiourea sulfate followed by saponification 4-(2-chloro-phenyl)-2-methylsulfanyl-pyrimidine-5-carboxylic acid as a white foam.

EXAMPLE 45

4-(2-Chloro-phenyl)-2-methanesulfonyl-pyrimidine-5-carboxylic Acid (3,5-bis-trifluoromethyl-benzyl)-methyl-amide In an analogous manner to that described in Example 15 there was obtained from 4-(2-chloro-phenyl)-2-methylsulfanyl-pyrimidine-5-carboxylic acid (3,5-bis-trifluoromethyl-benzyl)-methyl-amide and 3-chloroperbenzoicacid 4-(2-chloro-phenyl)-2-methanesulfonyl-pyrimidine-5-carboxylic acid (3,5-bis-trifluoromethyl-benzyl)-methyl-amide as a white foam, MS (ISP): 552.0 (M+H$^+$).

EXAMPLE 46

4-(2-Chloro-phenyl)-2-(4-methyl-piperazin-1-yl)-pyrimidine-5-carboxylic Acid (3,5-bis-trifluoromethyl-benzyl)-methyl-amide In an analogous manner to that described in Example 16 there was obtained from 4-(2-chloro-phenyl)-2-methylsulfonyl-pyrimidine-5-carboxylic acid (3,5-bis-trifluoromethyl-benzyl)-methyl-amide and 1-methylpiperazin 4-(2-chloro-phenyl)-2-(4-methyl-piperazin-1-yl)-pyrimidine-5-carboxylic acid (3,5-bis-trifluoromethyl-benzyl)-methyl-amide as a white foam, MS (ISP): 572.1 (M+H$^+$), which was treated with fumaric acid in the usual way to give 4-(2-chloro-phenyl)-2-(4-methyl-piperazin-1-yl)-pyrimidine-5-carboxylic acid (3,5-bis-trifluoromethyl-benzyl)-methyl-amide fumarate (1:1), m.p. 174.8–175.8°.

EXAMPLE 47

(3R,5S)-4-(2-Chloro-phenyl)-2-(3,5-dimethyl-piperazin-1-yl)-pyrimidine-5-carboxylic Acid (3,5-bis-trifluoromethyl-benzyl)-methyl-amide In an analogous manner to that described in Example 20 there was obtained from 4-(2-chloro-phenyl)-2-methylsulfonyl-pyrimidine-5-carboxylic acid (3,5-bis-trifluoromethyl-benzyl)-methyl-amide and cis-2,6-dimethylpiperazine (3R,5S)-4-(2-chloro-phenyl)-2-(3,5-dimethyl-piperazin-1-yl)-pyrimidine-5-carboxylic acid (3,5-bis-trifluoromethyl-benzyl)-methyl-amide as a white foam, MS (ISP): 586.1 (M+H$^+$).

EXAMPLE 48

4-(2-Chloro-phenyl)-2-piperazin-1-yl-pyrimidine-5-carboxylic Acid (3,5-bis-trifluoromethyl-benzyl)-methyl-amide In an analogous manner to that described in Example 19 there was obtained from 4-(2-chloro-phenyl)-2- methylsulfonyl-pyrimidine-5-carboxylic acid (3,5-bis-trifluoromethyl-benzyl)-methyl-amide and piperazine 4-(2-chloro-phenyl)-2-piperazin-1-yl-pyrimidine-5-carboxylic acid (3,5-bis-trifluoromethyl-benzyl)-methyl-amide as a white foam, MS (ISP): 558.2 (M+H$^+$), which was treated with fumaric acid in the usual way to give 4-(2-chloro-phenyl)-2-piperazin-1-yl-pyrimidine-5-carboxylic acid (3,5-bis-trifluoromethyl-benzyl)-methyl-amide fumarate (1:1), m.p. 123–126°.

EXAMPLE 49

4-(2-Chloro-phenyl)-2-morpholin-4-yl-pyrimidine-5-carboxylic Acid (3,5-bis-trifluoromethyl-benzyl)-methyl-amide In an analogous manner to that described in Example 18 there was obtained from 4-(2-chloro-phenyl)-2-methylsulfonyl-pyrimidine-5-carboxylic acid (3,5-bis-trifluoromethyl-benzyl)-methyl-amide and morpholine 4-(2-chloro-phenyl)-2-morpholin-4-yl-pyrimidine-5-carboxylic acid (3,5-bis-trifluoromethyl-benzyl)-methyl-amide as a white foam, MS (ISP): 559.1 (M+H$^+$).

EXAMPLE 50

4-(2-Chloro-phenyl)-2-(2-dimethylamino-ethylamino)-pyrimidine-5-carboxylic Acid (3,5-bis-trifluoromethyl-benzyl)-methyl-amide In an analogous manner to that described in Example 21 there was obtained from 4-(2-chloro-phenyl)-2-methylsulfonyl-pyrimidine-5-carboxylic acid (3,5-bis-trifluoromethyl-benzyl)-methyl-amide and 2-dimethylaminoethylamin 4-(2-chloro-phenyl)-2-(2-dimethylamino-ethylamino)-pyrimidine-5-carboxylic acid (3,5-bis-trifluoromethyl-benzyl)-methyl-amide as a white foam, MS (ISP): 560.2 (M+H$^+$).

EXAMPLE 51

4-(2-Chloro-phenyl)-2-(2-morpholin-4-yl-ethoxy)-pyrimidine-5-carboxylic Acid (3,5-bis-trifluoromethyl-benzyl)-methyl-amide In an analogous manner to that described in Example 24 there was obtained from 4-(2-chloro-phenyl)-2-methylsulfonyl-pyrimidine-5-carboxylic acid (3,5-bis-trifluoromethyl-benzyl)-methyl-amide and N-(2-hydroxyethyl)morpholine 4-(2-chloro-phenyl)-2-(2-morpholin-4-yl-ethoxy)-pyrimidine-5-carboxylic acid (3,5-bis-trifluoromethyl-benzyl)-methyl-amide as a white foam, MS (ISP): 603.0 (M+H$^+$).

EXAMPLE 52

4-(2-Chloro-phenyl)-2-(2-dimethylamino-ethoxy)-pyrimidine-5-carboxylic Acid (3,5-bis-trifluoromethyl-benzyl)-methyl-amide In an analogous manner to that described in Example 26 there was obtained from 4-(2-chloro-phenyl)-2-methylsulfonyl-pyrimidine-5-carboxylic acid (3,5-bis-trifluoromethyl-benzyl)-methyl-amide and 2-dimethylamino-ethanol 4-(2-chloro-phenyl)-2-(2-dimethylamino-ethoxy)-pyrimidine-5-carboxylic acid (3,5-bis-trifluoromethyl-benzyl)-methyl-amide as a colorless oil, MS (ISP): 561.2 (M+H$^+$).

EXAMPLE 53

4-(2-Chloro-phenyl)-2-(3-dimethylamino-propoxy)-pyrimidine-5-carboxylic Acid (3,5-bis-trifluoromethyl-benzyl)-methyl-amide In an analogous manner to that described in Example 27 there was obtained from 4-(2-chloro-phenyl)-2-methylsulfonyl-pyrimidine-5-carboxylic acid (3,5-bis-trifluoromethyl-benzyl)-methyl-amide and 2-dimethylamino-propanol 4-(2-chloro-phenyl)-2-(3-dimethylamino-propoxy)-pyrimidine-5-carboxylic acid (3,5-bis-trifluoromethyl-benzyl)-methyl-amide as a colorless oil, MS (ISP): 575.1 (M+H$^+$).

EXAMPLE 54

2-Methylsulfanyl-4-o-tolyl-pyrimidine-5-carboxylic Acid (3,5-bis-trifluoromethyl-benzyl)-methyl-amide In an analogous manner to that described in Example 37c) there was obtained from 2-methylsulfanyl-4-o-tolyl-pyrimidine-5-carboxylic acid and (3,5-bis-trifluoromethyl-benzyl)-methyl-amine 2-methylsulfanyl-4-o-tolyl-pyrimidine-5-carboxylic acid (3,5-bis-trifluoromethyl-benzyl)-methyl-amide as a white foam, MS (EI): 499 (M$^+$).

The used 2-methylsulfanyl-4-o-tolyl-pyrimidine-5-carboxylic acid as the starting substance was obtained as follows:

In an analogous manner to that described in Example 37a), b) there was obtained from 2-(2-methyl-benzoyl)-3-dimethylamino-acrylic acid ethyl ester and S-methylisothiourea sulfate followed by saponification 2-methylsulfanyl-4-o-tolyl-pyrimidine-5-carboxylic acid as a white foam.

EXAMPLE 55

2-Methylsulfonyl-4-o-tolyl-pyrimidine-5-carboxylic Acid (3,5-bis-trifluoromethyl-benzyl)-methyl-amide In an analogous manner to that described in Example 15 there was obtained from 2-methylsulfanyl-4-o-tolyl-pyrimidine-5-carboxylic acid (3,5-bis-trifluoromethyl-benzyl)-methyl-amide and 3-chloroperbenzoicacid 2-methylsulfonyl-4-o-tolyl-pyrimidine- 5-carboxylic acid (3,5-bis-trifluoromethyl-benzyl)-methyl-amide as a white foam, MS (ISP): 532.1 (M+H$^+$).

EXAMPLE 56

2-(4-Methyl-piperazin-1-yl)-4-o-tolyl-pyrimidine-5-carboxylic Acid (3,5-bis-trifluoromethyl-benzyl)-methyl-amide In an analogous manner to that described in Example 16 there was obtained from 2-methylsulfonyl-4-o-tolyl-pyrimidine-5-carboxylic acid (3,5-bis-trifluoromethyl-benzyl)-methyl-amide and 1-methylpiperazin 2-(4-methyl-piperazin-1-yl)-4-o-tolyl-pyrimidine-5-carboxylic acid (3,5-bis-trifluoromethyl-benzyl)-methyl-amide as a white foam, MS (ISP): 552.1 (M+H$^+$), which was treated with fumaric acid in the usual way to give 2-(4-methyl-piperazin-1-yl)-4-o-tolyl-pyrimidine-5-carboxylic acid (3,5-bis-trifluoromethyl-benzyl)-methyl-amide fumarate (1:1), m.p. 151.5–152.5°.

EXAMPLE 57

(3R,5S)-2-(3,5-Dimethyl-piperazin-1-yl)-4-o-tolyl-pyrimidine-5-carboxylic Acid (3,5-bis-trifluoromethyl-benzyl)-methyl-amide In an analogous manner to that described in Example 20 there was obtained from 2-methylsu lfonyl-4-o-tolyl-pyrimidine-5-carboxylic acid (3,5-bis-trifluoromethyl-benzyl)-methyl-amide and cis-2,6-dimethylpiperazine (3R, 5S)-2-(3,5-dimethyl-piperazin-1-yl)-4-o-tolyl-pyrimidine-5-carboxylic acid (3,5-bis-trifluoromethyl-benzyl)-methyl-amide as a white foam, MS (ISP): 566.3 (M+H$^+$), which was treated with fumaric acid in the usual way to give (3R,5S)-2-(3,5-dimethyl-piperazin-1-yl)-4-o-tolyl-pyrimidine-5-carboxylic acid (3,5-bis-trifluoromethyl-benzyl)-methyl-amide fumarate (1:0.5), m.p. 203.5–204.5°.

EXAMPLE 58

2-Piperazin-1-yl-4-o-tolyl-pyrimidine-5-carboxylic Acid (3,5-bis-trifluoromethyl-benzyl)-methyl-amide In an analogous manner to that described in Example 19 there was obtained from 2-methylsulfonyl-4-o-tolyl-pyrimidine-5-carboxylic acid (3,5-bis-trifluoromethyl-benzyl)-methyl-amide and piperazine 2-piperazin-1-yl-4-o-tolyl-pyrimidine-5-carboxylic acid (3,5-bis-trifluoromethyl-benzyl)-methyl-amide as a white foam, MS (ISP): 538.3 (M+H$^+$), which was treated with fumaric acid in the usual way to give 2-piperazin-1-yl-4-o-tolyl-pyrimidine-5-carboxylic acid (3,5-bis-trifluoromethyl-benzyl)-methyl-amide fumarate (1:1), m.p. 149.5–151.5°.

EXAMPLE 59

2-Morpholin-4-yl-4-o-tolyl-pyrimidine-5-carboxylic Acid (3,5-bis-trifluoromethyl-benzyl)-methyl-amide In an analogous manner to that described in Example 18 there was obtained from 2-methylsulfonyl-4-o-tolyl-pyrimidine-5-carboxylic acid (3,5-bis-trifluoromethyl-benzyl)-methyl-amide and morpholin 2-morpholin-4-yl-4-o-tolyl-pyrimidine-5-carboxylic acid (3,5-bis-trifluoromethyl-benzyl)-methyl-amide as a white foam, MS (EI): 538 (M$^+$).

EXAMPLE 60

2-(2-Dimethylamino-ethoxy)-4-o-tolyl-pyrimidine-5-carboxylic Acid (3,5-bis-trifluoromethyl-benzyl)-methyl-amide In an analogous manner to that described in Example 26 there was obtained from 2-methylsulfonyl-4-o-tolyl-pyrimidine-5-carboxylic acid (3,5-bis-trifluoromethyl-benzyl)-methyl-amide and 2-dimethylamino-ethanol 2-(2-dimethylamino-ethoxy)-4-o-tolyl-pyrimidine-5-carboxylic acid (3,5-bis-trifluoromethyl-benzyl)-methyl-amide as a colorless oil, MS (ISP): 541.2 (M+H$^+$).

EXAMPLE 61

2-(3-Dimethylamino-propoxy)-4-o-tolyl-pyrimidine-5-carboxylic Acid (3,5-bis-trifluoromethyl-benzyl)-methyl-amide In an analogous manner to that described in Example 27 there was obtained from 2-methylsulfonyl-4-o-tolyl-pyrimidine-5-carboxylic acid (3,5-bis-trifluoromethyl-benzyl)-methyl-amide and 2-dimethylamino-propanol 2-(3-dimethylamino-propoxy)-4-o-tolyl-pyrimidine-5-carboxylic acid (3,5-bis-trifluoromethyl-benzyl)-methyl-amide as a colorless oil, MS (ISP): 555.2 (M+H$^+$).

EXAMPLE 62

4-(2-Methoxy-phenyl)-2-methylsulfanyl-pyrimidine-5-carboxylic Acid (3,5-bis-trifluoromethyl-benzyl)-methyl-amide In an analogous manner to that described in Example 37c) there was obtained from 4-(2-methoxy-phenyl)-2-methylsulfanyl-pyrimidine-5-carboxylic acid and (3,5-bis-trifluoromethyl-benzyl)-methyl-amine 4-(2-methoxy-phenyl)-2-methylsulfanyl-pyrimidine-5-carboxylic acid (3,5-bis-trifluoromethyl-benzyl)-methyl-amide as a white foam, MS (EI): 515 (M$^+$). The 4-(2-methoxy-phenyl)-2-methylsulfanyl-pyrimidine-5-carboxylic acid used as the starting substance was obtained as follows:

In an analogous manner to that described in Example 37a), b) there was obtained from 2-(2-methoxy-benzoyl)-3-dimethylamino-acrylic acid ethyl ester and S-methylisothiourea sulfate followed by saponification 4-(2-methoxy-phenyl)-2-methylsulfanyl-pyrimidine-5-carboxylic acid as a white foam.

EXAMPLE 63

4-(2-Methoxy-phenyl)-2-methylsulfonyl-pyrimidine-5-carboxylic Acid (3,5-bis-trifluoromethyl-benzyl)-methyl-amide In an analogous manner to that described in Example 15 there was obtained from 4-(2-methoxy-phenyl)-2-methylsulfanyl-pyrimidine-5-carboxylic acid (3,5-bis-trifluoromethyl-benzyl)-methyl-amide and 3-chloroperbenzoicacid 4-(2-methoxy-phenyl)-2-methylsulfonyl-pyrimidine-5-carboxylic acid (3,5-bis-trifluoromethyl-benzyl)-methyl-amide as a white foam, MS (ISP): 548.1 (M+H$^+$).

EXAMPLE 64

4-(2-Methoxy-phenyl)-2-(4-methyl-piperazin-1-yl)-pyrimidine-5-carboxylic Acid (3,5-bis-trifluoromethyl-benzyl)-methyl-amide In an analogous manner to that described in Example 16 there was obtained from 4-(2-methoxy-phenyl)-2-methylsulfonyl-pyrimidine-5-carboxylic acid (3,5-bis-trifluoromethyl-benzyl)-methyl-amide and 1-methylpiperazin 4-(2-methoxy-phenyl)-2-(4-methyl-piperazin-1-yl)-pyrimidine-5-carboxylic acid (3,5-bis-trifluoromethyl-benzyl)-methyl-amide as a white foam, MS (ISP): 568.5 (M+H$^+$).

EXAMPLE 65

(3R,5S)-2-(3,5-Dimethyl-piperazin-1-yl)-4-(2-methoxy-phenyl)-pyrimidine-5-carboxylic Acid (3,5-bis-trifluoromethyl-benzyl)-methyl-amide In an analogous manner to that described in Example 20 there was obtained from 4-(2-methoxy-phenyl)-2-methylsulfonyl-pyrimidine-5-carboxylic acid (3,5-bis-trifluoromethyl-benzyl)-methyl-amide and cis-2,6-dimethylpiperazine (3R,5S)-2-(3,5-dimethyl-piperazin-1-yl)-4-(2-methoxy-phenyl)-pyrimidine-5-carboxylic acid (3,5-bis-trifluoromethyl-benzyl)-methyl-amide as a white foam, MS (ISP): 582.2 (M+H$^+$).

EXAMPLE 66

4-(2-Methoxy-phenyl)-2-piperazin-1-yl-pyrimidine-5-carboxylic Acid (3,5-bis-trifluoromethyl-benzyl)-methyl-amide In an analogous manner to that described in Example 19 there was obtained from 4-(2-methoxy-phenyl)-2-methylsulfonyl-pyrimidine-5-carboxylic acid (3,5-bis-trifluoromethyl-benzyl)-methyl-amide and piperazine 4-(2-methoxy-phenyl)- 2-piperazin-1-yl-pyrimidine-5- carboxylic acid (3,5-bis-trifluoromethyl-benzyl)-methyl-amide as a white foam, MS (ISP): 554.2 (M+H$^+$).

EXAMPLE 67

4-(2-Methoxy-phenyl)-2-morpholin-4-yl-pyrimidine-5-carboxylic Acid (3,5-bis-trifluoromethyl-benzyl)-methyl-amide In an analogous manner to that described in Example 18 there was obtained from 4-(2-methoxy-phenyl)-2-methylsulfonyl-pyrimidine-5-carboxylic acid (3,5-bis-trifluoromethyl-benzyl)-methyl-amide and morpholin 4-(2-methoxy-phenyl)-2-morpholin-4-yl-pyrimidine-5-carboxylic acid (3,5-bis-trifluoromethyl-benzyl)-methyl-amide as a white foam, m.p. 190.8–192.0°.

EXAMPLE 68

4-(4-Fluoro-phenyl)-2-methylsulfanyl-pyrimidine-5-carboxylic Acid (3,5-bis-trifluoromethyl-benzyl)-methyl-amide In an analogous manner to that described in Example 37c) there was obtained from 4-(4-fluoro-phenyl)-2-methylsulfanyl-pyrimidine-5-carboxylic acid and (3,5-bis-trifluoromethyl-benzyl)-methyl-amine 4-(4-fluoro-phenyl)-2-methylsulfanyl-pyrimidine-5-carboxylic acid (3,5-bis-trifluoromethyl-benzyl)-methyl-amide as a white foam, MS (EI): 503 (M$^+$).

EXAMPLE 69

4-(4-Fluoro-phenyl)-2-methylsulfonyl-pyrimidine-5-carboxylic Acid (3,5-bis-trifluoromethyl-benzyl)-methyl-amide In an analogous manner to that described in Example 15 there was obtained from 4-(4-fluoro-phenyl)-2-methylsulfanyl-pyrimidine-5-carboxylic acid (3,5-bis-trifluoromethyl-benzyl)-methyl-amide and 3-chloroperbenzoicacid 4-(4-fluoro-phenyl)-2-methylsulfonyl-pyrimidine-5-carboxylic acid (3,5-bis-trifluoromethyl-benzyl)-methyl-amide as a white foam, MS (EI): 535 (M$^+$).

EXAMPLE 70

4-(4-Fluoro-phenyl)-2-(4-methyl-piperazin-1-yl)-pyrimidine-5-carboxylic Acid (3,5-bis-trifluoromethyl-benzyl)-methyl-amide In an analogous manner to that described in Example 16 there was obtained from 4-(4-fluoro-phenyl)-2-methylsulfonyl-pyrimidine-5-carboxylic acid (3,5-bis-trifluoromethyl-benzyl)-methyl-amide and 1-methylpiperazin 4-(4-fluoro-phenyl)-2-(4-methyl-piperazin-1-yl)-pyrimidine-5-carboxylic acid (3,5-bis-trifluoromethyl-benzyl)-methyl-amide as a white foam, MS (EI): 555 (M$^+$), which was treated with fumaric acid in the usual way to give 4-(4-fluoro-phenyl)-2-(4-methyl-piperazin-1-yl)-pyrimidine-5-carboxylic acid (3,5-bis-trifluoromethyl-benzyl)-methyl-amide fumarate (1:1), m.p. 144.5–145.5°.

EXAMPLE 71

(3R,5S)-2-(3,5-Dimethyl-piperazin-1-yl)-4-(4-fluoro-phenyl)-pyrimidine-5-carboxylic Acid (3,5-bis-trifluoromethyl-benzyl)-methyl-amide In an analogous manner to that described in Example 20 there was obtained from 4-(4-fluor-phenyl)-2-methylsulfonyl-pyrimidine-5-carboxylic acid (3,5-bis-trifluoromethyl-benzyl)-methyl-amide and cis-2,6-dimethylpiperazine (3R,5S)-2-(3,5-dimethyl-piperazin-1-yl)-4-(4-fluoro-phenyl)-pyrimidine-5-carboxylic acid (3,5-bis-trifluoromethyl-benzyl)-methyl-amide as a white foam, MS (ISP): 570.2 (M+H$^+$), which was treated with fumaric acid in the usual way to give (3R,5S)-2-(3,5-dimethyl-piperazin-1-yl)-4-(4-fluoro-phenyl)-pyrimidine-5-carboxylic acid (3,5-bis-trifluoromethyl-benzyl)-methyl-amide fumarate (1:0.5), m.p. 220–223°.

EXAMPLE 72

4-(4-Fluor-phenyl)-2-piperazin-1-yl-pyrimidine-5-carboxylic Acid (3,5-bis-trifluoromethyl-benzyl)-methyl-amide In an analogous manner to that described in Example 19 there was obtained from 4-(4-fluor-phenyl)-2-methylsulfonyl-pyrimidine-5-carboxylic acid (3,5-bis-trifluoromethyl-benzyl)-methyl-amide and piperazine 4-(4-fluor-phenyl)-2-piperazin-1-yl-pyrimidine-5-carboxylic acid (3,5-bis-trifluoromethyl-benzyl)-methyl-amide as a white foam, MS (ISP): 542.2 (M+H$^+$), which was treated with fumaric acid in the usual way to give 4-(4-fluoro-phenyl)-2-piperazin-1-yl-pyrimidine-5-carboxylic acid (3,5-bis-trifluoromethyl-benzyl)-methyl-amide fumarate (1:1), m.p. 155–158° C.

EXAMPLE 73

4-(4-Fluor-phenyl)-2-morpholin-4-yl-pyrimidine-5-carboxylic Acid (3,5-bis-trifluoromethyl-benzyl)-methyl-amide In an analogous manner to that described in Example 18 there was obtained from 4-(4-fluoro-phenyl)-2-methylsulfonyl-pyrimidine-5-carboxylic acid (3,5-bis-trifluoromethyl-benzyl)-methyl-amide and Morpholin 4-(4-fluor-phenyl)-2-morpholin-4-yl-pyrimidine-5-carboxylic acid (3,5-bis-trifluoromethyl-benzyl)-methyl-amide as a white foam, MS (ISP): 543.2 (M+H$^+$).

EXAMPLE 74

4-(2-Fluoro-phenyl)-2-methylsulfanyl-pyrimidine-5-carboxylic Acid (3,5-bis-trifluoromethyl-benzyl)-methyl-amide In an analogous manner to that described in Example 37c) there was obtained from 4-(2-fluoro-phenyl)-2-methylsulfanyl-pyrimidine-5-carboxylic acid and (3,5-bis-trifluoromethyl-benzyl)-methyl-amine 4-(2-fluoro-phenyl)-2-methylsulfanyl-pyrimidine- 5-carboxylic acid (3,5-bis-trifluoromethyl-benzyl)-methyl-amide as a white solid, m.p. 109.5–110°.

The 4-(2-fluoro-phenyl)-2-methylsulfanyl-pyrimidine-5-carboxylic acid used as the starting substance was obtained as follows:

In an analogous manner to that described in Example 37a), b) there was obtained from 2-(2-fluoro-benzoyl)-3-dimethylamino-acrylic acid ethyl ester and S-methylisothiourea sulfate followed by saponification 4-(2-fluoro-phenyl)-2-methylsulfanyl-pyrimidine-5-carboxylic acid as a white foam.

EXAMPLE 75

4-(2-Fluoro-phenyl)-2-methylsulfonyl-pyrimidine-5-carboxylic Acid (3,5-bis-trifluoromethyl-benzyl)-methyl-amide In an analogous manner to that described in Example 15 there was obtained from 4-(2-fluoro-phenyl)-2- methylsulfanyl-pyrimidine-5-carboxylic acid (3,5-bis-trifluoromethyl-benzyl)-methyl-amide and 3-chloroperbenzoicacid 4-(2-fluoro-phenyl)-2-methylsulfonyl-pyrimidine-5-carboxylic acid (3,5-bis-trifluoromethyl-benzyl)-methyl-amide as a white foam, MS (ISP): 536.2 (M+H$^+$).

EXAMPLE 76

4-(2-Fluoro-phenyl)-2-(4-methyl-piperazin-1-yl)-pyrimidine-5-carboxylic Acid (3,5-bis-trifluoromethyl-benzyl)-methyl-amide In an analogous manner to that described in Example 16 there was obtained from 4-(2-fluoro-phenyl)-2-methylsulfonyl-pyrimidine-5-carboxylic acid (3,5-bis-trifluoromethyl-benzyl)-methyl-amide and 1-methylpiperazin 4-(2-fluoro-phenyl)-2-(4-methyl-piperazin-1-yl)-pyrimidine-5-carboxylic acid (3,5-bis-trifluoromethyl-benzyl)-methyl-amide as a white foam, MS (ISP): 556.1 (M+H$^+$).

EXAMPLE 77

(3R,5S)-2-(3,5-Dimethyl-piperazin-1-yl)-4-(2-fluoro-phenyl)-pyrimidine-5-carboxylic Acid (3,5-bis-trifluoromethyl-benzyl)-methyl-amide In an analogous manner to that described in Example 20 there was obtained from 4-(2-fluoro-phenyl)-2-methylsulfonyl-pyrimidine-5-carboxylic acid (3,5-bis-trifluoromethyl-benzyl)-methyl-amide and cis-2,6-dimethylpiperazine (3R,5S)-2-(3,5-dimethyl-piperazin-1-yl)-4-(2-fluoro-phenyl)-pyrimidine-5-carboxylic acid (3,5-bis-trifluoromethyl-benzyl)-methyl-amide as a white foam, MS (ISP): 570.2 (M+H$^+$).

EXAMPLE 78

4-(4-Fluor-phenyl)-2-piperazin-1-yl-pyrimidine-5-carboxylic Acid (3,5-bis-trifluoromethyl-benzyl)-methyl-amide In an analogous manner to that described in Example 19 there was obtained from 4-(2-fluoro-phenyl)-2-methylsulfonyl-pyrimidine-5-carboxylic acid (3,5-bis-trifluoromethyl-benzyl)-methyl-amide and piperazine 4-(4-fluor-phenyl)-2-piperazin-1-yl-pyrimidine-5-carboxylic acid (3,5-bis-trifluoromethyl-benzyl)-methyl-amide as a white foam, MS (ISP): 542.2 (M+H$^+$), which was treated with fumaric acid in the usual way to give 4-(2-fluoro-phenyl)-2-piperazin-1-yl-pyrimidine-5-carboxylic acid (3,5-bis-trifluoromethyl-benzyl)-methyl-amide fumarate (1:1), m.p. 124.8–125.1°.

EXAMPLE 79

4-(2-Fluor-phenyl)-2-morpholin-4-yl-pyrimidine-5-carboxylic Acid (3,5-bis-trifluoromethyl-benzyl)-methyl-amide In an analogous manner to that described in Example 18 there was obtained from 4-(2-fluoro-phenyl)-2-methylsulfonyl-pyrimidine-5-carboxylic acid (3,5-bis-trifluoromethyl-benzyl)-methyl-amide and morpholin 4-(2-fluor-phenyl)-2-morpholin-4-yl-pyrimidine-5-carboxylic acid (3,5-bis-trifluoromethyl-benzyl)-methyl-amide as a white foam, MS (EI): 542 (M$^+$).

EXAMPLE 80

4-(4-Fluoro-2-methyl-phenyl)-2-methylsulfanyl-pyrimidine-5-carboxylic Acid (3,5-bis-trifluoromethyl-benzyl)-methyl-amide In an analogous manner to that described in Example 37c) there was obtained from 4-(4-fluoro-2-methyl-phenyl)-2-methylsulfanyl-pyrimidine-5-carboxylic acid and (3,5-bis-trifluoromethyl-benzyl)-methyl-amine 4-(4-fluoro-2-methyl-phenyl)-2-methylsulfanyl-pyrimidine-5-carboxylic acid (3,5-bis-trifluoromethyl-benzyl)-methyl-amide as a white solid, MS (EI): 517 (M$^+$). The 4-(4-fluoro-2-methyl-phenyl)-2-methylsulfanyl-pyrimidine-5-carboxylic acid used as the starting substance was obtained as follows:

In an analogous manner to that described in Example 37a), b) there was obtained from 2-(4-fluoro-2-methyl-benzoyl)-3-dimethylamino-acrylic acid ethyl ester and S-methylisothiourea sulfate followed by saponification 4-(4-fluoro-2-methyl-phenyl)-2-methylsulfanyl-pyrimidine-5-carboxylic acid as a white foam.

EXAMPLE 81

4-(4-Fluoro-2-methyl-phenyl)-2-methylsulfonyl-pyrimidine-5-carboxylic Acid (3,5-bis-trifluoromethyl-benzyl)-methyl-amide In an analogous manner to that described in Example 15 there was obtained from 4-(4-fluoro-2-methyl-phenyl)-2-methylsulfanyl-pyrimidine-5-carboxylic acid (3,5-bis-trifluoromethyl-benzyl)-methyl-amide and 3-chloroperbenzoicacid 4-(4-fluoro-2-methyl-phenyl)-2-methylsulfonyl-pyrimidine-5-carboxylic acid (3,5-bis-trifluoromethyl-benzyl)-methyl-amide as a white foam, MS (EI): 549 (M$^+$).

EXAMPLE 82

4-(4-Fluoro-2-methyl-phenyl)-2-(4-methyl-piperazin-1-yl)-pyrimidine-5-carboxylic Acid (3,5-bis-trifluoromethyl-benzyl)-methyl-amide In an analogous manner to that described in Example 16 there was obtained from 4-(4-fluoro-2-methyl-phenyl)-2-methylsulfonyl-pyrimidine-5-carboxylic acid (3,5-bis-trifluoromethyl-benzyl)-methyl-amide and 1-methylpiperazin 4-(4-fluoro-2-methyl-phenyl)-2-(4-methyl-piperazin-1-yl)-pyrimidine-5-carboxylic acid (3,5-bis-trifluoromethyl-benzyl)-methyl-amide as a white foam, MS (ISP): 570.2 (M+H$^+$), which was treated with fumaric acid in the usual way to give 4-(4-fluoro-2-methyl-phenyl)-2-piperazin-1-yl-pyrimidine-5-carboxylic acid (3,5-bis-trifluoromethyl-benzyl)-methyl-amide fumarate (1:1), m.p. 185.0–186.5°.

EXAMPLE 83

(3R,5S)-2-(3,5-Dimethyl-piperazin-1-yl)-4-(4-fluoro-2-methyl-phenyl)-pyrimidine-5-carboxylic Acid (3,5-bis-trifluoromethyl-benzyl)-methyl-amide In an analogous manner to that described in Example 20 there was obtained from 4-(4-fluor-2-methyl-phenyl)-2-methylsulfonyl-pyrimidine-5-carboxylic acid (3,5-bis-trifluoromethyl-benzyl)-methyl-amide and cis-2,6-dimethylpiperazine (3R,5S)-2-(3,5-dimethyl-piperazin-1-yl)-4-(4-fluoro-2-methyl-phenyl)-pyrimidine-5-carboxylic acid (3,5-bis-trifluoromethyl-benzyl)-methyl-amide as a white foam, MS (ISP): 548.1 (M+H$^+$), which was treated with fumaric acid in the usual way to give (3R,5S)-2-(3,5-dimethyl-piperazin-1-yl)-4-(4-fluoro-2-methyl-phenyl)-pyrimidine-5-carboxylic acid (3,5-bis-trifluoromethyl-benzyl)-methyl-amide fumarate (1:0.5), m.p. 228–230°.

EXAMPLE 84

4-(4-Fluor-2-methyl-phenyl)-2-piperazin-1-yl-pyrimidine-5-carboxylic Acid (3,5-bis-trifluoromethyl-benzyl)-methyl-amide In an analogous manner to that described in Example 19 there was obtained from 4-(4-fluor-2-methyl-phenyl)-2- methylsulfonyl-pyrimidine-5-carboxylic acid (3,5-bis-trifluoromethyl-benzyl)-methyl-amide and piperazine 4-(4-Fluor-2-methyl-phenyl)-2-piperazin-1-yl-pyrimidine-5-carboxylic acid (3,5-bis-trifluoromethyl-benzyl)-methyl-amide as a white foam, MS (ISP): 556.1 (M+H$^+$), which was treated with fumaric acid in the usual way to give 4-(2-fluoro-phenyl)-2-piperazin-1-yl-pyrimidine-5-carboxylic acid (3,5-bis-trifluoromethyl-benzyl)-methyl-amide fumarate (1:1), m.p. 143–145°.

EXAMPLE 85

4-(4-Fluoro-2-methyl-phenyl)-2-morpholin-4-yl-pyrimidine-5-carboxylic Acid (3,5-bis-trifluoromethyl-benzyl)-methyl-amide In an analogous manner to that described in Example 18 there was obtained from 4-(4-fluoro-2-methyl-phenyl)-2-methylsulfonyl-pyrimidine-5-carboxylic acid (3,5-bis-trifluoromethyl-benzyl)-methyl-amide and morpholin 4-(4-fluoro-2-methyl-phenyl)-2-morpholin-4-yl-pyrimidine-5-carboxylic acid (3,5-bis-trifluoromethyl-benzyl)-methyl-amide as a white foam, MS (ISP): 557.1 (M+H$^+$).

EXAMPLE 86

2-Methylsulfanyl-4-naphthalen-1-yl-pyrimidine-5-carboxylic Acid (3,5-bis-trifluoromethyl-benzyl)-methyl-amide In an analogous manner to that described in Example 37c) there was obtained from 2-methylsulfanyl-4-naphthalen-1-yl-pyrimidine-5-carboxylic acid and (3,5-bis-trifluoromethyl-benzyl)-methyl-amine 2-methylsulfanyl-4-naphthalen-1-yl-pyrimidine-5-carboxylic acid (3,5-bis-trifluoromethyl-benzyl)-methyl-amide as a white foam, MS (EI): 535 (M$^+$).

The 2-methylsulfanyl-4-naphthalen-1-yl-pyrimidine-5-carboxylic acid used as the starting substance was obtained as follows:

In an analogous manner to that described in Example 37a), b) there was obtained from 3-dimethylamino-2-(naphthalene-1-carbonyl)-acrylic acid ethyl ester and S-methylisothiourea sulfate followed by saponification 2-methylsulfanyl-4-naphthalen-1-yl-pyrimidine-5-carboxylic acid as a white foam.

EXAMPLE 87

2-Methylsulfonyl-4-naphthalen-1-yl-pyrimidine-5-carboxylic Acid (3,5-bis-trifluoromethyl-benzyl)-methyl-amide In an analogous manner to that described in Example 15 there was obtained from 2-methylsulfanyl-4-naphthalen-1-yl-pyrimidine-5-carboxylic acid (3,5-bis-trifluoromethyl-benzyl)-methyl-amide and 3-chloroperbenzoicacid 2-methylsulfonyl-4-naphthalen-1-yl-pyrimidine-5-carboxylic acid (3,5-bis-trifluoromethyl-benzyl)-methyl-amide as a white foam, MS (ISP): 568.1 (M+H$^+$).

EXAMPLE 88

2-(4-Methyl-piperazin-1-yl)-4-naphthalen-1-yl-pyrimidine-5-carboxylic Acid (3,5-bis-trifluoromethyl-benzyl)-methyl-amide In an analogous manner to that described in Example 16 there was obtained from 2-methylsulfonyl-4-naphthalen-1-yl-pyrimidine-5-carboxylic acid (3,5-bis-trifluoromethyl-benzyl)-methyl-amide and 1-methylpiperazin 2-(4-methyl-piperazin-1-yl)-4-naphthalen-1-yl-pyrimidine-5-carboxylic acid (3,5-bis-trifluoromethyl-benzyl)-methyl-amide as a white solid, m.p. 170.6–170.9°.

EXAMPLE 89

(3R,5S)-2-(3,5-Dimethyl-piperazin-1-yl)-4-naphthalen-1-yl-pyrimidine-5-carboxylic Acid (3,5-bis-trifluoromethyl-benzyl)-methyl-amide In an analogous manner to that described in Example 20 there was obtained from 2-methylsulfonyl-4-naphthalen-1-yl-pyrimidine-5-carboxylic acid (3,5-bis-trifluoromethyl-benzyl)-methyl-amide and cis-2,6-dimethylpiperazine (3R,5S)-2-(3,5-dimethyl-piperazin-1-yl)-4-naphthalen-1-yl-pyrimidine-5-carboxylic acid (3,5-bis-trifluoromethyl-benzyl)-methyl-amide a white foam, MS (ISP): 602.1 (M+H$^+$), which was treated with fumaric acid in the usual way to give (3R,5S)-2-(3,5-dimethyl-piperazin-1-yl)-4-naphthalen-1-yl-pyrimidine-5-carboxylic acid (3,5-bis-trifluoromethyl-benzyl)-methyl-amide fumarate (1:0.5), m.p. 247–249°.

EXAMPLE 90

4-Naphthalen-1-yl-2-piperazin-1-yl-pyrimidine-5-carboxylic Acid (3,5-bis-trifluoromethyl-benzyl)-methyl-amide In an analogous manner to that described in Example 19 there was obtained from 2-methylsulfonyl-4-naphthalen-1-yl-pyrimidine-5-carboxylic acid (3,5-bis-trifluoromethyl-benzyl)-methyl-amide and piperazine 4-naphthalen-1-yl-2-piperazin-1-yl-pyrimidine-5-carboxylic acid (3,5-bis-trifluoromethyl-benzyl)-methyl-amide as a white foam, MS (ISP): 574.2 (M+H$^+$), which was treated with fumaric acid in the usual way to give 4-naphthalen-1-yl-2-piperazin-1-yl-pyrimidine-5-carboxylic acid (3,5-bis-trifluoromethyl-benzyl)-methyl-amide fumarate (1:1), m.p. 176–178°.

EXAMPLE 91

2-Morpholin-4-yl-4-naphthalen-1-yl-pyrimidine-5-carboxylic Acid (3,5-bis-trifluoromethyl-benzyl)-methyl-amide In an analogous manner to that described in Example 18 there was obtained from 2-methylsulfonyl-4-naphthalen-1-yl-pyrimidine-5-carboxylic acid (3,5-bis-trifluoromethyl-benzyl)-methyl-amide and morpholin 2-morpholin-4-yl-4-naphthalen-1-yl-pyrimidine-5-carboxylic acid (3,5-bis-trifluoromethyl-benzyl)-methyl-amide as a white foam, MS (ISP): 575.1 (M+H$^+$).

EXAMPLE 92

4-Phenyl-2-pyridin-3-yl-pyrimidine-5-carboxylic Acid (3,5-bis-trifluoromethyl-benzyl)-methyl-eamide In an analogous manner to that described in Example 3d) there was obtained from 4-phenyl-2-pyridin-3-yl-pyrimidine-5-carboxylic acid and (3,5-bis-trifluoromethyl-benzyl)-methyl-amine 4-phenyl-2-pyridin-3-yl-pyrimidine-5-carboxylic acid (3,5-bis-trifluoromethyl-benzyl)-methyl-amide as a colorless solid, m.p. 127°–128°.

The 4-phenyl-2-pyridin-3-yl-pyrimidine-5-carboxylic acid used as the starting substance was obtained as follows:

In an analogous manner to that described in example 3b) starting from 2-benzoyl-3-dimethylamino-acrylic acid ethyl ester and 3-amidinopyridine hydrochloride, followed by saponification as described in example 3c) there was obtained 4-phenyl-2-pyridin-3-yl-pyrimidine-5-carboxylic acid, MS (EI): 277 (M+).

EXAMPLE 93

4-(2-Chloro-4-fluorophenyl)-2-methylsulfanyl-pyrimidine-5-carboxylic Acid (3,5-bis-trifluoromethyl-benzyl)-methyl-amide In an analogous manner to that described in Example 37c) there was obtained from 4-(2-chloro-4-fluoro-phenyl)-2-methylsulfanyl-pyrimidine-5-carboxylic acid and (3,5-bis-trifluoromethyl-benzyl)-methyl-amine 4-(2-chloro-4-fluoro-phenyl)-2-methylsulfanyl-pyrimidine-5-carboxylic acid (3,5-bis-trifluoromethyl-benzyl)-methyl-amide as a white foam, MS (ISP): 538.1 (M+H+).

The 4-(2-chloro-4-fluoro-phenyl)-2-methylsulfanyl-pyrimidine-5-carboxylic acid used as the starting substance was obtained as follows:

In an analogous manner to that described in Example 37a), b) there was obtained from 2-(2-chloro-4-fluoro-benzoyl)-3-dimethylamino-acrylic acid ethyl ester and S-methylisothiourea sulfate followed by saponification 4-(2-chloro-4-fluoro-phenyl)-2-methylsulfanyl-pyrimidine-5-carboxylic acid as a white foam.

EXAMPLE 94

4-(2-Chloro-4-fluoro-phenyl)-2-methylsulfonyl-pyrimidine-5-carboxylic Acid (3,5-bis-trifluoromethyl-benzyl)-methyl-amide In an analogous manner to that described in Example 15 there was obtained from 4-(2-chloro-4-fluoro-phenyl)-2-methylsulfanyl-pyrimidine-5-carboxylic acid (3,5-bis-trifluoromethyl-benzyl)-methyl-amide and 3-chloroperbenzoicacid 4-(2-chloro-4-fluoro-phenyl)-2-methylsulfonyl-pyrimidine-5-carboxylic acid (3,5-bis-trifluoromethyl-benzyl)-methyl-amide as a white foam, MS (ISP): 570.1 (M+H+).

EXAMPLE 95

4-(2-Chloro-4-fluoro-phenyl)-2-(4-methyl-piperazin-1-yl)-pyrimidine-5-carboxylic Acid (3,5-bis-trifluoromethyl-benzyl)-methyl-amide In an analogous manner to that described in Example 16 there was obtained from 4-(2-chloro-4-fluoro-phenyl)-2-methylsulfonyl-pyrimidine-5-carboxylic acid (3,5-bis-trifluoromethyl-benzyl)-methyl-amide and 1-methylpiperazine 4-(2-chloro-4-fluoro-phenyl)-2-(4-methyl-piperazin-1-yl)-pyrimidine-5-carboxylic acid (3,5-bis-trifluoromethyl-benzyl)-methyl-amide as a white foam, MS (ISP): 590.1 (M+H+).

EXAMPLE 96

4-(2-Chloro-4-fluoro-phenyl)-2-morpholin-4-yl-pyrimidine-5-carboxylic Acid (3,5-bis-trifluoromethyl-benzyl)-methyl-amide In an analogous manner to that described in Example 18 there was obtained from 4-(2-chloro-4-fluoro-phenyl)-2-methylsulfonyl-pyrimidine-5-carboxylic acid (3,5-bis-trifluoromethyl-benzyl)-methyl-amide and morpholine 4-(2-chloro-4-fluoro-phenyl)-2-morpholin-4-yl-pyrimidine-5-carboxylic acid (3,5-bis-trifluoromethyl-benzyl)-methyl-amide as a white foam, MS (ISP): 577.0 (M+H+).

EXAMPLE 97

4-(2-Chloro-4-fluoro-phenyl)-2-piperazin-1-yl-pyrimidine-5-carboxylic Acid (3,5-bis-trifluoromethyl-benzyl)-methyl-amide In an analogous manner to that described in Example 19 there was obtained from 4-(2-chloro-4-fluoro-phenyl)-2-methylsulfonyl-pyrimidine-5-carboxylic acid (3,5-bis-trifluoromethyl-benzyl)-methyl-amide and piperazine 4-(2-chloro-4-fluoro-phenyl)-2-piperazin-1-yl-pyrimidine-5-carboxylic acid (3,5-bis-trifluoromethyl-benzyl)-methyl-amide as a white foam, MS (ISP): 576.0 (M+H+).

EXAMPLE 98

4-(2-Chloro-4-fluoro-phenyl)-2-(2-dimethylamino-ethoxy)-pyrimidine-5-carboxylic Acid (3,5-bis-trifluoromethyl-benzyl)-methyl-amide In an analogous manner to that described in Example 26 there was obtained from 4-(2-chloro-4-fluoro-phenyl)-2-methylsulfonyl-pyrimidine-5-carboxylic acid (3,5-bis-trifluoromethyl-benzyl)-methyl-amide and 2-dimethylamino-ethanol 4-(2-chloro-4-fluoro-phenyl)-2-(2-dimethylamino-ethoxy)-pyrimidine-5-carboxylic acid (3,5-bis-trifluoromethyl-benzyl)-methyl-amide as a colorless oil, MS (ISP): 579.1 (M+H+).

EXAMPLE 99

4-(2-Chloro-4-fluoro-phenyl)-2-(3-dimethylamino-propoxy)-pyrimidine-5-carboxylic Acid (3,5-bis-trifluoromethyl-benzyl)-methyl-amide In an analogous manner to that described in Example 27 there was obtained from 4-(2-chloro-4-fluoro-phenyl)-2-methylsulfonyl-pyrimidine-5-carboxylic acid (3,5-bis-trifluoromethyl-benzyl)-methyl-amide and 2-dimethylamino-propanol 4-(2-chloro-4-fluoro-phenyl)-2-(3-dimethylamino-propoxy)-pyrimidine-5-carboxylic acid (3,5-bis-trifluoromethyl-benzyl)-methyl-amid as a colorless oil, MS (ISP): 593.1 (M+H+).

EXAMPLE 100

4-(2-Chloro-4-fluoro-phenyl)-2-(2-morpholin-4-yl-ethoxy)-pyrimidine-5-carboxylic Acid (3,5-bis-trifluoromethyl-benzyl)-methyl-amide In an analogous manner to that described in Example 24 there was obtained from 4-(2-chloro-4-fluoro-phenyl)-2-methylsulfonyl-pyrimidine-5-carboxylic acid (3,5-bis-trifluoromethyl-benzyl)-methyl-amide and N-(2-hydroxyethyl)morpholine 4-(2-chloro-4-fluoro-phenyl)-2-(2-morpholin-4-yl-ethoxy)-pyrimidine-5-carboxylic acid (3,5-bis-trifluoromethyl-benzyl)-methyl-amide as a pale yellow oil, MS (ISP): 621.0 (M+H+).

EXAMPLE 101

2-Methylsulfanyl-4-o-tolyl-pyrimidine-5-carboxylic Acid (3,5-dimethoxy-benzyl)-methyl-amide To a solution of 3.00 g (11.52 mmol) 2-methylsulfanyl-4-o-tolyl-pyrimidine-5-carboxylic acid in 70 ml $CH_2Cl_2$ 3.21 ml (23.05 mmol) triethylamine, 1.55 g (11.52 mmol) 1-hydroxybenzotriazole and 2.20 g (11.52 mmol) N-(3-dimethylaminopropyl)-N'-ethylcarbodiimide hydrochloride 2.29 g (12.68 mmol) (3,5-dimethoxy-benzyl)-methyl-amine were added. The reaction mixture was stirred for 16 hrs. The reaction mixture was diluted with 100 ml $CH_2Cl_2$, washed with 100 ml 0.5N HCl and 100 ml $H_2O$. The aqueous layers were backextracted with 100 ml $CH_2Cl_2$. The combined organic layers were dried ($MgSO_4$), filtered and evaporated. The residue was purified by chromatography ($SiO_2$, $CH_2Cl_2$/MeOH) to give 4.20 g (86%) 2-methylsulfanyl-4-o-tolyl-pyrimidine-5-carboxylic acid (3,5-dimethoxy-benzyl)-methyl-amide as a colorless oil, MS (ISP): 424.1 (M+H$^+$).

EXAMPLE 102

2-Methanesulfonyl-4-o-tolyl-pyrimidine-5-carboxylic Acid (3,5-dimethoxy-benzyl)-methyl-amide To a solution of 4.00 g (9.44 mmol) 2-methylsulfanyl-4-o-tolyl-pyrimidine-5-carboxylic acid (3,5-dimethoxy-benzyl)-methyl-amide in 100 ml $CH_2Cl_2$ 5.82 g (23.61 mmol) 3-chloroperbenzoic acid (70%) was added at 5° and the reaction mixture stirred for 3 hrs. at RT. After addition of 100 ml sat. $NaHCO_3$-solution, the layers were separated, the organic phase washed with sat. $NaHCO_3$-solution, dried ($Na_2SO_4$), filtered and evaporated. The residue was purified by chromatography ($SiO_2$, $CH_2Cl_2$/ethyl acetate 4:1) to give 2.00 g (46%) 2-methanesulfonyl-4-o-tolyl-pyrimidine-5-carboxylic acid (3,5-dimethoxy-benzyl)-methyl-amide as a colorless foam, MS (ISP): 456.5 (M+H$^+$).

EXAMPLE 103

2-(4-Methyl-piperazin-1-yl)-4-o-tolyl-pyrimidine-5-carboxylic Acid (3,5-dimethoxy-benzyl)-methyl-amide In an analogous manner to that described in Example 16 there was obtained from 2-methanesulfonyl-4-o-tolyl-pyrimidine-5-carboxylic acid (3,5-dimethoxy-benzyl)-methyl-amide and 1-methylpiperazine 2-(4-methyl-piperazin-1-yl)-4-o-tolyl-pyrimidine-5-carboxylic acid (3,5-dimethoxy-benzyl)-methyl-amide as a colorless oil, MS (ISP): 476.3 (M+H$^+$).

EXAMPLE 104

2-Morpholin-4-yl-4-o-tolyl-pyrimidine-5-carboxylic Acid (3,5-dimethoxy-benzyl)-methyl-amide In an analogous manner to that described in Example 18 there was obtained from 2-methanesulfonyl-4-o-tolyl-pyrimidine-5-carboxylic acid (3,5-dimethoxy-benzyl)-methyl-amide and morpholine 2-morpholin-4-yl-4-o-tolyl-pyrimidine-5-carboxylic acid (3,5-dimethoxy-benzyl)-methyl-amide as a colorless foam, MS (ISP): 463.3 (M+H$^+$).

EXAMPLE 105

2-(2-Dimethylamino-ethylamino)-4-o-tolyl-pyrimidine-5-carboxylic Acid (3,5-dimethoxy-benzyl)-methyl-amide In an analogous manner to that described in Example 21 there was obtained from 2-methanesulfonyl-4-o-tolyl-pyrimidine-5-carboxylic acid (3,5-dimethoxy-benzyl)-methyl-amide and 2-dimethylaminoethylamine 2-(2-dimethylamino-ethylamino)-4-o-tolyl-pyrimidine-5-carboxylic acid (3,5-dimethoxy-benzyl)-methyl-amide as a pale yellow oil, MS (ISP): 464.4 (M+H$^+$).

EXAMPLE 106

2-(2-Dimethylamino-ethoxy)-4-o-tolyl-pyrimidine-5-carboxylic Acid (3,5-dimethoxy-benzyl)-methyl-amide In an analogous manner to that described in Example 26 there was obtained from 2-methanesulfonyl-4-o-tolyl-pyrimidine-5-carboxylic acid (3,5-dimethoxy-benzyl)-methyl-amide and 2-dimethylaminoethanol 2-(2-dimethylamino-ethoxy)-4-o-tolyl-pyrimidine-5-carboxylic acid (3,5-dimethoxy-benzyl)-methyl-amide as a pale yellow oil, MS (EI): 465.3 (M+H$^+$).

EXAMPLE 107

2-Methylsulfanyl-4-o-tolyl-pyrimidine-5-carboxylic Acid (3,5-dimethyl-benzyl)-methyl-amide To a solution of 2.60 g (9.99 mmol) 2-methylsulfanyl-4-o-tolyl-pyrimidine-5-carboxylic acid in 70 ml $CH_2Cl_2$ 2.78 ml (19.98 mmol) triethylamine, 1.34 g (9.99 mmol) 1-hydroxybenzotriazole and 1.91 g (9.99 mmol) N-(3-dimethylaminopropyl)-N'-ethylcarbodiimide hydrochloride 1.78 g (11.99 mmol) (3,5-dimethoxy-benzyl)-methyl-amine were added. The reaction mixture was stirred for 16 hrs. The reaction mixture was diluted with 100 ml $CH_2Cl_2$, washed with 100 ml 0.5N HCl and 100 ml $H_2O$. The aqueous layers were backextracted with 100 ml $CH_2Cl_2$. The combined organic layers were dried ($MgSO_4$), filtered and evaporated. The residue was purified by chromatography ($SiO_2$, $CH_2Cl_2$/MeOH 40:1) to give 3.20 g (82%) 2-methylsulfanyl-4-o-tolyl-pyrimidine-5-carboxylic acid (3,5-dimethyl-benzyl)-methyl-amide as a pale yellow oil, MS (EI): 391 (M$^+$).

EXAMPLE 108

2-Methanesulfonyl-4-o-tolyl-pyrimidine-5-carboxylic Acid (3,5-dimethyl-benzyl)-methyl-amide To a solution of 3.20 g (8.17 mmol) 2-methylsulfanyl-4-o-tolyl-pyrimidine-5-carboxylic acid (3,5-dimethyl-benzyl)-methyl-amide in 70 ml $CH_2Cl_2$ 3.52 g (20.43 mmol) 3-chloroperbenzoic acid (70%) was added at 5° and the reaction mixture stirred for 3 hrs. at RT. After addition of 100 ml sat. $NaHCO_3$-solution, the layers were separated, the organic phase washed with sat. $NaHCO_3$-solution, dried ($Na_2SO_4$), filtered and evaporated. The residue was purified by chromatography ($SiO_2$, $CH_2Cl_2$/ethyl acetate 4:1) to give 2.55 g (73%) 2-methanesulfonyl-4-o-tolyl-pyrimidine-5-carboxylic acid (3,5-dimethyl-benzyl)-methyl-amide as a colorless foam, MS (EI): 423 (M$^+$).

EXAMPLE 109

2-(4-Methyl-piperazin-1-yl)-4-o-tolyl-pyrimidine-5-carboxylic Acid (3,5-dimethyl-benzyl)-methyl-amide In an analogous manner to that described in Example 16 there was obtained from 2-methanesulfonyl-4-o-tolyl-pyrimidine-5-carboxylic acid (3,5-dimethyl-benzyl)-methyl-amide and 1-methylpiperazine 2-(4-methyl-piperazin-1-yl)-4-o-tolyl-pyrimidine-5-carboxylic acid (3,5-dimethyl-benzyl)-methyl-amide as a colorless foam, MS (ISP): 444.5 (M+H$^+$).

EXAMPLE 110

2-Morpholin-4-yl-4-o-tolyl-pyrimidine-5-carboxylic Acid (3,5-dimethyl-benzyl)-methyl-amide In an analogous manner to that described in Example 18 there was obtained from 2-methanesulfonyl-4-o-tolyl-pyrimidine-5-carboxylic acid (3,5-dimethyl-benzyl)-methyl-amide and morpholine 2-morpholin-4-yl-4-o-tolyl-pyrimidine-5-carboxylic acid (3,5-dimethyl-benzyl)-methyl-amide as a colorless foam, MS (EI): 430 (M$^+$).

EXAMPLE 111

2-(2-Dimethylamino-ethoxy)-4-o-tolyl-pyrimidine-5-carboxylic Acid (3,5-dimethyl-benzyl)-methyl-amide In an analogous manner to that described in Example 26 there was obtained from 2-methanesulfonyl-4-o-tolyl-pyrimidine-5-carboxylic acid (3,5-dimethyl-benzyl)-methyl-amide and 2-dimethylaminoethanol 2-(2-dimethylamino-ethoxy)-4-o-tolyl-pyrimidine-5-carboxylic acid (3,5-dimethyl-benzyl)-methyl-amide as a pale yellow oil, MS (ISP): 433.5 (M+H$^+$).

EXAMPLE 112

2-(3,5-Bis-trifluoromethyl-phenyl)-N-methyl-N-(2-methylsulfanyl-4-o-tolyl-pyrimidin-5-yl)-isobutyramide a) (2-Methylsulfanyl-4-o-tolyl-pyrimidin-5-yl)-carbamic Acid tert.-butyl Ester To a solution of 2.33 g (8.95 mmol) 2-methylsulfanyl-4-o-tolyl-pyrimidine-5-carboxylic acid, 1.25 ml triethylamine (8.95 mmol) and 1.68 ml (17.9 mmol) t-butanol in 30 ml THF, 1.97 ml (8.95 mmol) diphenylphosphorylazide were added and the resulting solution heated at reflux for 12 hrs. After evaporation of the solvent, the residue was distributed between CH$_2$Cl$_2$ and H$_2$O. The aqueous phase was extracted twice with CH$_2$Cl$_2$. The combined organic layers were dried (Na$_2$SO$_4$), filtered and evaporated. The residue was purified by chromatography (SiO$_2$, CH$_2$Cl$_2$/ethyl acetate 15:1) to give 1.95 g (65%) (2-methylsulfanyl-4-o-tolyl-pyrimidin-5-yl)-carbamic acid tert.-butyl ester as a colorless solid, MS (TSP): 331 (M$^+$).

b) Methyl-(2-methylsulfanyl-4-o-tolyl-pyrimidin-5-yl)-carbamic Acid tert.-butyl Ester To a solution of 1.9 g (5.73 mmol) (2-methylsulfanyl-4-o-tolyl-pyrimidin-5-yl)-carbamic acid tert.-butyl ester in 15 ml N,N-dimethylformamide 0.29 g (7.45 mmol) sodiumhydride (60% dispersion in mineraloil) was added and the reaction mixture stirred for 1 hr. After the addition of 0.57ml (9.17 mmol) methyl iodide at 0°, the reaction mixture was stirred for 3 hrs. The reaction mixture was distributed between 75 ml H$_2$O, 75 ml brine and 75 ml CH$_2$Cl$_2$. The phases were separated, the aqueous layer washed twice with 75 ml CH$_2$Cl$_2$. The combined organic layers were dried (Na$_2$SO$_4$), filtered and evaporated. The residue was purified by chromatography (SiO$_2$, CH$_2$Cl$_2$/ethyl acetate 15:1) to give 1.95 g (98%) methyl-(2-methylsulfanyl-4-o-tolyl-pyrimidin-5-yl)-carbamic acid tert.-butyl ester as a colorless oil. MS (TSP): 345 (M$^+$).

c) Methyl-(2-methylsulfanyl-4-o-tolyl-pyrimidin-5-yl)-amine

A solution of 1.95 g (5.64 mmol) methyl-(2-methylsulfanyl-4-o-tolyl-pyrimidin-5-yl)-carbamic acid tert-butyl ester in 30 ml MeOH/HCl (2N) was stirred at 50° for 3 hr. After evaporation of the solvent, the residue was distributed between 40 ml 1N NaOH and 40 ml CH$_2$Cl$_2$. The phases were separated, the aqueous layer washed twice with 50 ml CH$_2$Cl$_2$. The combined organic layers were dried (Na$_2$SO$_4$), filtered and evaporated. The residue was purified by chromatography (SiO$_2$, CH$_2$Cl$_2$/ethyl acetate 10:1) to give 1.30 g (94%) methyl-(2-methylsulfanyl-4-o-tolyl-pyrimidin-5-yl)-amine as a white solid, MS (EI): 245 (M$^+$).

d) 2-(3,5-Bis-trifluoromethyl-phenyl)-N-methyl-N-(2-methylsulfanyl-4-o-tolyl-pyrimidin-5-yl)-isobutyramide To a solution of 1.30 g (5.3 mmol) methyl-(2-methylsulfanyl-4-o-tolyl-pyrimidin-5-yl)-amine and 1.36 ml (7.95 mmol) N-ethyldiisopropylamine in 15 ml CH$_2$Cl$_2$ a solution of 1.30 g (5.3 mmol) 2-(3,5-bis-trifluoromethyl-phenyl)-2-methyl-propionyl chloride in 5 ml CH$_2$Cl$_2$ were added and the reaction mixture stirred for 24 hrs. at RT. The reaction mixture was poured onto 50 ml 0.5 N NaOH-solution. The phases were separated, the aqueous layer washed twice with 50 ml CH$_2$Cl$_2$. The combined organic layers were dried (Na$_2$SO$_4$), filtered and evaporated. The residue was purified by chromatography (SiO$_2$, CH$_2$Cl$_2$/ethyl acetate 10:1) to give 2.30 g (82%) 2-(3,5-bis-trifluoromethyl-phenyl)-N-methyl-N-(2-methylsulfanyl-4-o-tolyl-pyrimidin-5-yl)-isobutyramide as a white solid, m.p. 124–125°, MS (ISP): 528.2 (M+H$^+$).

EXAMPLE 113

2-(3,5-Bis-trifluoromethyl-phenyl)-N-(2-methanesulfonyl-4-o-tolyl-pyrimidin-5-yl)-N-methyl-isobutyramide To a solution of 2.20 g (4.17 mmol) 2-methylsulfanyl-4-phenyl-pyrimidine-5-carboxylic acid (3,5-bis-trifluoromethyl-benzyl)-methyl-amide in 50 ml CH$_2$Cl$_2$ 2.57 g (10.43 mmol) 3-chloroperbenzoic acid (70%) was added at 50 and the reaction mixture stirred for 3 hrs. at RT. After addition of 100 ml sat. NaHCO$_3$-solution, the layers were separated, the organic phase washed with sat. NaHCO$_3$-solution, dried (Na$_2$SO$_4$), filtered and evaporated. The residue was purified by chromatography (SiO$_2$, CH$_2$Cl$_2$/ethyl acetate 10:1) to give 2.30 g (98%) 2-(3,5-bis-trifluoromethyl-phenyl)-N-(2-methanesuffonyl-4-o-tolyl-pyrimidin-5-yl)-N-methyl-isobutyramide as a colorless foam, MS (ISP): 560.2 (M+H$^+$).

EXAMPLE 114

2-(3,5-Bis-trifluoromethyl-phenyl)-N-methyl-N-[2-(4-methyl-piperazin-1-yl)-4-o-tolyl-pyrimidin-5-yl]-isobutyramide To a solution of 0.5 g (0.89 mmol) 2-(3,5-bis-trifluoromethyl-phenyl)-N-(2-methanesulfonyl-4-o-tolyl-pyrimidin-5-yl)-N-methyl-isobutyramide in 10 ml dioxane 0.25 ml (2.23 mmol) 1-methylpiperazine was added. The reaction mixture was stirred for 16 hrs. After evaporation of the solvent, the residue was distributed between 50 ml CH$_2$Cl$_2$ and 50 ml H$_2$O. The aqueous layer was extracted with 50 ml CH$_2$Cl$_2$, the combined organic layers dried (MgSO$_4$), filtered and evaporated. The residue was purified by chromatography (SiO$_2$, CH$_2$Cl$_2$/MeOH/NH$_4$OH 110:10:1) to give 0.37 g (71%) 2-(3,5-bis-trifluoromethyl-phenyl)-N-methyl-N-[2-(4-methyl-piperazin-1-yl)-4-o-tolyl-pyrimidin-5-yl]-isobutyramide as a colorless solid, m.p. 149°151°, MS (ISP): 580.1 (M+H$^+$).

EXAMPLE 115

2-(3,5-Bis-trifluoromethyl-phenyl)-N-methyl-N-(2-morpholin-4-yl-4-o-tolyl-pyrimidin-5-yl)-isobutyramide To a solution of 0.4 g (0.71 mmol) 2-(3,5-bis-trifluoromethyl-phenyl)-N-(2-methanesulfonyl-4-o-tolylpyrimidin-5-yl)-N-methyl-isobutyramide in 10 ml dioxane 0.19 ml (2.14 mmol) morpholine was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/ethyl acetate) to give 0.34 g (84%) 2-(3,5-bis-trifluoromethyl-phenyl)-N-methyl-N-(2-morpholin-4-yl-4-o-tolyl-pyrimidin-5-yl)-isobutyramide as a colorless solid, m.p. 151°152°, MS (ISP): 567.1 (M+H$^+$).

EXAMPLE 116

2-(3,5-Bis-trifluoromethyl-phenyl)-N-[2-(2-dimethylamino-ethylamino)-4-o-tolyl-pyrimidin-5-yl]-N-methyl-isobutyramide To a solution of 0.35 g (0.63 mmol) 2-(3,5-bis-trifluoromethyl-phenyl)-N-(2-methanesulfonyl-4-o-tolyl-pyrimidin-5-yl)-N-methyl-isobutyramide in 10 ml dioxane 0.20 ml (1.88 mmol) 2-dimethylaminoethylamine was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH/$NH_4OH$) to give 0.23 g (64%) 2-(3,5-bis-trifluoromethyl-phenyl)-N-[2-(2-dimethylamino-ethylamino)-4-o-tolyl-pyrimidin-5-yl]-N-methyl-isobutyramide as a colorless solid, m.p. 143°–144°, MS (ISP): 568.3 (M+H$^+$).

EXAMPLE 117

2-(3,5-Bis-trifluoromethyl-phenyl)-N-[2-(2-dimethylamino-ethoxy)-4-o-tolyl-pyrimidin-5-yl]-N-methyl-isobutyramide To a solution of 0.4 g (0.71 mmol) 2-(3,5-bis-trifluoromethyl-phenyl)-N-(2-methanesulfonyl-4-o-tolyl-pyrimidin-5-yl)-N-methyl-isobutyramide in 15 ml acetonitrile 0.09 ml (0.93 mmol) 2-dimethylamino-ethanol and 1.17 g (3.57 mmol) $Cs_2CO_3$ were added. The reaction mixture was stirred for 16 hrs. After evaporation of the solvent, the residue was distributed between 40 ml $CH_2Cl_2$ and 40 ml $H_2O$. The aqueous layer was extracted with 40 ml $CH_2Cl_2$, the combined organic layers dried ($MgSO_4$), filtered and evaporated. The residue was purified by chromatography ($SiO_2$, $CH_2Cl_2$/MeOH/$NH_4OH$ 110:10:1) to give 0.36 g (88%) 2-(3,5-bis-trifluoromethyl-phenyl)-N-[2-(2-dimethylamino-ethoxy)-4-o-tolyl-pyrimidin-5-yl]-N-methyl-isobutyramide as a colorless solid, m.p. 140°–141°, MS (ISP): 569.2 (M+H)$^+$.

EXAMPLE 118

2-(3,5-Bis-trifluoromethyl-phenyl)-N-methyl-N-[2-(2-morpholin-4-yl-ethoxy)-4-o-tolyl-pyrimidin-5-yl]-isobutyramide To a solution of 0.4 g (0.71 mmol) 2-(3,5-bis-trifluoromethyl-phenyl)-N-(2-methanesulfonyl-4-o-tolyl-pyrimidin-5-yl)-N-methyl-isobutyramide in 15 ml acetonitrile 0.12 g (0.93 mmol) N-(2-hydroxymethyl)-morpholine and 1.17 g (3.57 mmol) $Cs_2CO_3$ were added. The reaction mixture was stirred for 16 hrs. After evaporation of the solvent, the residue was distributed between 40 ml $CH_2Cl_2$ and 40 ml $H_2O$. The aqueous layer was extracted with 40 ml $CH_2Cl_2$, the combined organic layers dried ($MgSO_4$), filtered and evaporated. The residue was purified by chromatography ($SiO_2$, $CH_2Cl_2$/MeOH/$NH_4OH$ 110:10:1) to give 0.35 g (80%) 2-(3,5-bis-trifluoromethyl-phenyl)-N-methyl-N-[2-(2-morpholin-4-yl-ethoxy)-4-o-tolyl-pyrimidin-5-yl]-isobutyramide as a colorless foam, MS (ISP): 611.1 (M+H$^+$).

EXAMPLE A

Tablets of the following composition are manufactured in the usual manner:

| mg/tablet | |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

| mg/capsule | |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

| mg/supp. | |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

What is claimed is:
1. A compound of the formula

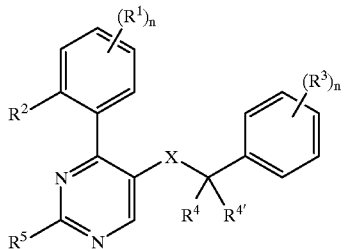

wherein
R¹ is hydrogen or halogen;
R² is hydrogen, halogen, lower alkyl or lower alkoxy;
R¹ and R² may together be —CH═C—CH═CH—, wherein R¹ and R² together with the two carbon ring atoms to which they are attached, form a fused ring;
R³ is halogen, trifluoromethyl, lower alkyl or lower alkoxy;
R⁴ and R⁴' are each independently hydrogen or lower alkyl;
R⁵ is lower alkyl, lower alkoxy, amino, phenyl, hydroxy-lower alkyl, cyano-lower alkyl, carbamoyl-lower alkyl, pyridyl, pyrimidyl, —(CH₂)$_n$-piperazinyl, —(CH₂)$_n$-piperazinyl which is substituted by one or two lower alkyl groups or by hydroxy-lower alkyl, —(CH₂)$_n$-morpholinyl, —(CH₂)$_n$-piperidinyl, —(CH₂)$_{n+1}$-imidazolyl, lower alkyl-sulfanyl, lower alkyl-sulfonyl, benzylamino, —NH—(CH₂)$_{n+1}$N(R⁴")₂, —(CH₂)$_{n+1}$N(R⁴")₂, —O—(CH₂)$_{n+1}$-morpholinyl, —O—(CH₂)$_{n+1}$-piperidinyl or —O—(CH₂)$_{n+1}$N(R⁴")₂, wherein R⁴" is hydrogen or lower alkyl; and
n is 0–2;
X is —C(O)N(R⁴")— or —N(R⁴")C(O)—;
and pharmaceutically acceptable acid addition salts thereof.

2. The compound according to claim 1, wherein X is —C(O)N(R⁴")—, R⁴" is methyl and R⁵ is piperazinyl or piperazinyl substituted by one or two methyl groups.

3. The compound according to claim 2, which is selected from the group consisting of:
4-(2-bromo-phenyl)-2-(4-methyl-piperazin-1-yl)-pyrimidine-5-carboxylic acid (3,5-bis-trifluoromethyl-benzyl)-methyl-amide,
(3R,5S)-4-(2-bromo-phenyl)-2-(3,5-dimethyl-piperazin-1-yl)-pyrimidine-5-carboxylic acid (3,5-bis-trifluoromethyl-benzyl)-methyl-amide,
4-(2-bromo-phenyl)-2-piperazin-1-yl-pyrimidine-5-carboxylic acid (3,5-bis-trifluoromethyl-benzyl)-methyl-amide,
4-(2-chloro-phenyl)-2-(4-methyl-piperazin-1-yl)-pyrimidine-5-carboxylic acid (3,5-bis-trifluoromethyl-benzyl)-methyl-amide,
(3R,5S)-4-(2-chloro-phenyl)-2-(3,5-dimethyl-piperazin-1-yl)-pyrimidine-5-carboxylic acid (3,5-bis-trifluoromethyl-benzyl)-methyl-amide,
4-(2-chloro-phenyl)-2-piperazin-1-yl-pyrimidine-5-carboxylic acid (3,5-bis-trifluoromethyl-benzyl)-methyl-amide,
2-(4-methyl-piperazin-1-yl)-4-o-tolyl-pyrimidine-5-carboxylic acid (3,5-bis-trifluoromethyl-benzyl)-methyl-amide,
(3R,5S)-2-(3,5-dimethyl-piperazin-1-yl)-4-o-tolyl-pyrimidine-5-carboxylic acid (3,5-bis-trifluoromethyl-benzyl)-methyl-amide,
2-piperazin-1-yl-4-o-tolyl-pyrimidine-5-carboxylic acid (3,5-bis-trifluoromethyl-benzyl)-methyl-amide,
4-(2-methoxy-phenyl)-2-(4-methyl-piperazin-1-yl)-pyrimidine-5-carboxylic acid (3,5-bis-trifluoromethyl-benzyl)-methyl-amide,
(3R,5S)-2-(3,5-dimethyl-piperazin-1-yl)-4-(2-methoxy-phenyl)-pyrimidine-5-carboxylic acid (3,5-bis-trifluoromethyl-benzyl)-methyl-amide,
4-(2-methoxy-phenyl)-2-piperazin-1-yl-pyrimidine-5-carboxylic acid (3,5-bis-trifluoromethyl-benzyl)-methyl-amide,
4-(4-fluoro-phenyl)-2-(4-methyl-piperazin-1-yl)-pyrimidine-5-carboxylic acid (3,5-bis-trifluoromethyl-benzyl)-methyl-amide,
4-(2-fluoro-phenyl)-2-(4-methyl-piperazin-1-yl)-pyrimidine-5-carboxylic acid (3,5-bis-trifluoromethyl-benzyl)-methyl-amide,
(3R,5S)-2-(3,5-dimethyl-piperazin-1-yl)-4-(2-fluoro-phenyl)-pyrimidine-5-carboxylic acid (3,5-bis-trifluoromethyl-benzyl)-methyl-amide,
4-(4-fluor-phenyl)-2-piperazin-1-yl-pyrimidine-5-carboxylic acid (3,5-bis-trifluoromethyl-benzyl)-methyl-amide,
4-(4-fluoro-2-methyl-phenyl)-2-(4-methyl-piperazin-1-yl)-pyrimidine-5-carboxylic acid (3,5-bis-trifluoromethyl-benzyl)-methyl-amide,
(3R,5S)-2-(3,5-dimethyl-piperazin-1-yl)-4-(4-fluoro-2-methyl-phenyl)-pyrimidine-5-carboxylic acid (3,5-bis-trifluoromethyl-benzyl)-methyl-amide,
4-(4-fluor-2-methyl-phenyl)-2-piperazin-1-yl-pyrimidine-5-carboxylic acid (3,5-bis-trifluoromethyl-benzyl)-methyl-amide,
2-(4-methyl-piperazin-1-yl)-4-naphthalen-1-yl-pyrimidine-5-carboxylic acid (3,5-bis-trifluoromethyl-benzyl)-methyl-amide,
(3R,5S)-2-(3,5-dimethyl-piperazin-1-yl)-4-naphthalen-1-yl-pyrimidine-5-carboxylic acid (3,5-bis-trifluoromethyl-benzyl)-methyl-amide, and
4-naphthalen-1-yl-2-piperazin-1-yl-pyrimidine-5-carboxylic acid (3,5-bis-trifluoromethyl-benzyl)-methyl-amide.

4. The compound according to claim 1, in which X is —C(O)N(R⁴")—, R⁴" is methyl and R⁵ is morpholinyl or —O(CH₂)₂-morpholinyl.

5. The compound according to claim 4, which is selected from the group consisting of:
4-(2-bromo-phenyl)-2-morpholin-4-yl-pyrimidine-5-carboxylic acid (3,5-bis-trifluoromethyl-benzyl)-methyl-amide,
4-(2-chloro-phenyl)-2-morpholin-4-yl-pyrimidine-5-carboxylic acid (3,5-bis-trifluoromethyl-benzyl)-methyl-amide,
4-(2-chloro-phenyl)-2-(2-morpholin-4-yl-ethoxy)-pyrimidine-5-carboxylic acid (3,5-bis-trifluoromethyl-benzyl)-methyl-amide,
2-morpholin-4-yl-4-o-tolyl-pyrimidine-5-carboxylic acid (3,5-bis-trifluoromethyl-benzyl)-methyl-amide,
4-(2-methoxy-phenyl)-2-morpholin-4-yl-pyrimidine-5-carboxylic acid (3,5-bis-trifluoromethyl-benzyl)-methyl-amide,
4-(4-fluoro-2-methyl-phenyl)-2-morpholin-4-yl-pyrimidine-5-carboxylic acid (3,5-bis-trifluoromethyl-benzyl)-methyl-amide, and
2-morpholin-4-yl-4-naphthalen-1-yl-pyrimidine-5-carboxylic acid (3,5-bis-trifluoromethyl-benzyl)-methyl-amide.

6. The compound according to claim 1, in which X is —C(O)N(R⁴")—, R⁴" is methyl and R⁵ is —NH(CH₂)₂N(CH₃)₂, —O(CH₂)₂N(CH₃)₂ or —O(CH₂)₃N(CH₃)₂.

7. The compound according to claim 6, which is selected from the group consisting of:
4-(2-chloro-phenyl)-2-(2-dimethylamino-ethylamino)-pyrimidine-5-carboxylic acid (3,5-bis-trifluoromethyl-benzyl)-methyl-amide,
4-(2-chloro-phenyl)-2-(2-dimethylamino-ethoxy)-pyrimidine-5-carboxylic acid (3,5-bis-trifluoromethyl-benzyl)-methyl-amide,
4-(2-chloro-phenyl)-2-(3-dimethylamino-propoxy)-pyrimidine-5-carboxylic acid (3,5-bis-trifluoromethyl-benzyl)-methyl-amide,
2-(2-dimethylamino-ethoxy)-4-o-tolyl-pyrimidine-5-carboxylic acid (3,5-bis-trifluoromethyl-benzyl)-methyl-amide, and
2-(3-dimethylamino-propoxy)-4-o-tolyl-pyrimidine-5-carboxylic acid (3,5-bis-trifluoromethyl-benzyl)-methyl-amide.

8. The compound according to claim 1, in which X is —N($R^{4"}$)C(O)—, $R^{4"}$ is methyl and $R^5$ is morpholinyl, piperazinyl, or piperazinyl substituted by lower alkyl.

9. The compound according to claim 8, which is selected form the group consisting of:
2-(3,5-bis-trifluoromethyl-phenyl)-N-methyl-N-[2-(4-methyl-piperazin-1-yl)-4-o-tolyl-pyrimidin-5-yl]-isobutyramide, and
2-(3,5-bis-trifluoromethyl-phenyl)-N-methyl-N-(2-morpholin-4-yl-4-o-tolyl-pyrimidin-5-yl)-isobutyramide.

10. A pharmaceutical composition comprising a compound according to claim 1 and at least one pharmaceutically acceptable excipient.

11. A method of treatment of a central nervous system disorder taken from the group consisting of depression, anxiety and psychosis in a patient in need of such treatment, comprising administering to the patient a compound in accordance with claim 1 in an effective amount between about 10 mg to about 1000 mg per day.

* * * * *